(12) United States Patent
Keel et al.

(10) Patent No.: US 8,983,604 B2
(45) Date of Patent: Mar. 17, 2015

(54) CLOSED-LOOP SYSTEMS AND METHODS FOR CONTROLLING NEUROSTIMULATION BASED ON FAR-FIELD CARDIAC SIGNALS SENSED BY A SPINAL CORD STIMULATION DEVICE

(71) Applicants: Allen Keel, San Diego, CA (US); Stuart Rosenberg, Castaic, CA (US); Rupinder Bharmi, Canyon Country, CA (US); Kyungmoo Ryu, Palmdale, CA (US); Edward Karst, Los Angeles, CA (US); Fujian Qu, San Jose, CA (US); Xiaoyi Min, Camarillo, CA (US); Yelena Nabutovsky, Sunnyvale, CA (US)

(72) Inventors: Allen Keel, San Diego, CA (US); Stuart Rosenberg, Castaic, CA (US); Rupinder Bharmi, Canyon Country, CA (US); Kyungmoo Ryu, Palmdale, CA (US); Edward Karst, Los Angeles, CA (US); Fujian Qu, San Jose, CA (US); Xiaoyi Min, Camarillo, CA (US); Yelena Nabutovsky, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/838,305

(22) Filed: Mar. 15, 2013

(65) Prior Publication Data
US 2014/0277278 A1 Sep. 18, 2014

(51) Int. Cl.
*A61N 1/365* (2006.01)
*A61N 1/36* (2006.01)

(52) U.S. Cl.
CPC ......... *A61N 1/36114* (2013.01); *A61N 1/36139* (2013.01)

USPC ........................ 607/18; 607/6; 607/7; 607/11

(58) Field of Classification Search
USPC ............................ 607/2–18, 25–28, 115–118
See application file for complete search history.

(56) References Cited

U.S. PATENT DOCUMENTS 7,805,196 B2   9/2010  Miesel et al.
8,275,457 B1 *  9/2012  Fischell et al. .................... 607/9

(Continued)

FOREIGN PATENT DOCUMENTS

WO         2006050309         5/2006

OTHER PUBLICATIONS

Liu, et al., "Thoracic Spinal Cord Stimulation Improves Cardiac Contractile Function and Myocardial Oxygen Consumption in a Porcine Model of Ischemic Heart Failure,"J Cardiovasc Electrophysiol, Col. pp. 1-7 (May 2012).

*Primary Examiner* — Allen Porter, Jr.
(74) *Attorney, Agent, or Firm* — Theresa A. Raymer

(57) ABSTRACT

Techniques are provided for controlling spinal cord stimulation (SCS) or other forms of neurostimulation. Far-field cardiac electrical signals are sensed using a lead of the SCS device and neurostimulation is selectively delivering using a set of adjustable SCS control parameters. Parameters representative of cardiac rhythm are derived from the far-field cardiac electrical signals. The parameters representative of cardiac rhythm are correlated with SCS control parameters to thereby map neurostimulation control settings to cardiac rhythm parameters. The delivery of further neurostimulation is then controlled based on the mapping of neurostimulation control settings to cardiac rhythm parameters to, for example, address any cardiovascular disorders detected based on the far-field cardiac signals. In this manner, a closed loop control system is provided to automatically adjust SCS control parameters to respond to changes in cardiac rhythm such as changes associated with ischemia, arrhythmia or heart failure.

31 Claims, 16 Drawing Sheets

(56) References Cited

U.S. PATENT DOCUMENTS

| | | |
|---|---|---|
| 2006/0095081 A1 | 5/2006 | Zhou |
| 2011/0144709 A1* | 6/2011 | Baynham et al. ............... 607/14 |
| 2013/0268016 A1* | 10/2013 | Xi et al. .......................... 607/17 |
| 2014/0039238 A1* | 2/2014 | Min et al. .......................... 600/9 |

\* cited by examiner

CLOSED-LOOP SYSTEMS AND METHODS FOR CONTROLLING NEUROSTIMULATION BASED ON FAR-FIELD CARDIAC SIGNALS SENSED BY A SPINAL CORD STIMULATION DEVICE

FIELD OF THE INVENTION

The invention generally relates to implantable neurostimulation devices and, in particular, to techniques for controlling spinal cord stimulation (SCS) to address cardiovascular disorders, pain or other conditions.

BACKGROUND OF THE INVENTION

SCS is a type of neurostimulation primarily intended to manage chronic pain, particularly within the back, neck, arms or legs. Benefits of SCS or other forms of neurostimulation may include: a reduction in pain; a reduction or elimination of the use of pain medications; and increased activity levels and an improved overall quality of life. Neurostimulation has been used to manage pain from failed back surgery syndrome or post-laminectomy syndrome and other neuropathies. To this end, an SCS system may be implanted within the body to deliver electrical pulses to nerves along the spinal cord. The SCS system typically includes a small generator device similar to a pacemaker but equipped to send electrical pulses to leads mounted along nerves near the spinal cord. The generator is usually implanted in the abdomen or buttock area. The stimulation leads may include thin wires or paddles for delivering electrical pulses to the nerves along the spinal cord. Thin wire leads, also referred to as percutaneous leads, may be implanted within the epidural space. Paddle leads are instead typically implanted during a surgical procedure where a small amount of bone is removed from one or more of the vertebra. An external controller, similar to a remote control, is provided to allow the patient to control or adjust the neurostimulation.

Although SCS devices are primarily intended to address pain, it would be desirable to enable such devices to also address cardiovascular disorders such as atrial or ventricular arrhythmias, ischemia or heart failure. At least some SCS systems have been developed for use with implantable cardiac rhythm management devices (CRMDs) for monitoring and addressing cardiac health. See, for example, the systems and techniques described in: U.S. Pat. No. 8,706,239 of Bharmi et al., filed May 31, 2012, entitled "Systems and Methods for Controlling Neurostimulation based on Regional Cardiac Performance for use by Implantable Medical Devices" See, also, systems and techniques described in: U.S. Publication No. 2013/0268016 of Xi et al., filed Apr. 9, 2012, entitled "Systems and Methods for Controlling Spinal Cord Stimulation to Improve Stimulation Efficacy for use by Implantable Medical Devices." Still further, see, U.S. Patent Publication 2006/0095081 of Zhou et al., entitled "Methods and Apparatus for Sensing Cardiac Activity via Neurological Stimulation Therapy System or Medical Electrical Lead."

It would be desirable to provide improved systems and techniques for controlling SCS based on cardiac signals, particularly systems and techniques that need not be used in conjunction with a CRMD, and at least some of the aspects of the present invention are directed to that general end.

SUMMARY OF THE INVENTION

In an exemplary embodiment, a method is provided for use with an implantable neurostimulation system. Briefly, far-field cardiac electrical signals are sensed using a lead of the neurostimulation device and neurostimulation is selectively delivered using a set of adjustable control parameters. Parameters representative of cardiac rhythm are derived from the far-field cardiac electrical signals. The parameters representative of cardiac rhythm are correlated with neurostimulation control parameters to thereby map neurostimulation control settings to cardiac rhythm parameters. The delivery of further neurostimulation is then controlled or adjusted based on the mapping of neurostimulation control settings to cardiac rhythm parameters to, for example, address any cardiovascular disorders detected based on the far-field cardiac signals. In this manner, a closed loop control system is provided that allows for neurostimulation control parameters to be automatically adjusted to respond to changes in cardiac rhythm such as changes associated with ischemia, arrhythmia or heart failure.

In an illustrative example, the neurostimulation system is an SCS system having a lead with various electrodes for implant within an epidural space of an upper thoracic region of the patient. The SCS device is equipped to sense both neural electrical signals and far-field cardiac electrical signals and to discriminate therebetween. In one specific example, the SCS device has a cardiac sense amplifier and a separate neural sense amplifier. In an example where a single wideband sense amplifier is instead provided, the SCS device selectively filters a frequency spectrum sensed by the wideband amplifier to separate cardiac signals from neural signals. Still further, the SCS device may identify and distinguish various cardiac events such as atrial depolarization events (P-waves); ventricular depolarization events (R-waves); and ventricular repolarization events (T-waves) using one or more sensing vectors, i.e. a particular combination of electrodes with which signals are sensed. (In SCS examples where Octrode™ leads are employed, two sets of octrodes are used in the epidural space to span the lower thoracic zone for SCS. Each Octrode™ has eight electrodes. An Octrode™ lead is a type of linear eight electrode percutaneous lead provided by St Jude Medical™. When using such a lead, a vector is defined as a combination of any one or multiple of these "rings" in combination with the device "can" or housing to form the anode and cathode.) Different cardiac events can be distinguished based, for example, on signal amplitude, signal slope, signal morphology, sensing vector or sensing electrode spacing. For example, a vector spanning the atria of the heart will more readily sense P-waves; whereas a vector remote from the atria will typically not sense P-waves and so a comparison of far-field signals derived from those different vectors may be used to discriminate P-waves from R-waves. The relative spacing of electrode pairs can also provide a basis for distinguishing R-waves from P-waves, with relatively wider inter-electrode spacing providing signals that emphasize R-waves as opposed to P-waves. That is, the device may be equipped to record or obtain cardiac signals from a different electrode configuration (i.e. "vector") than used for the neural sensing electrode configuration to help distinguish cardiac signals from neural signals. For example, for an Octrode™ lead, the distal electrode to "Can" is a relatively large field vector that picks up the R-wave; whereas the distal to "Ring 8" is a narrower field vector that picks up atrial activity.

In the illustrative example, the SCS device uses P-waves, R-waves and other features of the cardiac signal to detect heart rate variability (HRV), atrial and ventricular arrhythmias, prolonged QT intervals, ischemia or other cardiac conditions or parameters. Insofar as HRV is concerned, the device preferably detects: high frequency (HF) components of HRV; low frequency (LF) components of HRV; and very low frequency (VLF) components of HRV, as well as a pNN50 statistical value. The device then correlates the various HRV parameters with different sets of neurostimulation control parameters to generate a map, atlas or library of data to allow for closed-loop control of SCS. For example, the clinician may program the device with a target HRV value and then the neurostimulation control parameters are automatically adjusted by the device in an effort to achieve the target value. As another example, if tachycardia is detected, the device examines the map relating neurostimulation control settings to HRV to identify a control setting configuration associated with a parasympathetic response within the patient and then delivers further neurostimulation using that particular control setting to address the tachycardia. In this regard, a parasympathetic response is generally associated with an HRV exhibiting: a high pNN50 value; a relatively high HF; and a relatively low LF/HF ratio. Hence, the device examines the mapping database to identify a particular set of SCS control parameters sufficient to achieve those HRV characteristics and then delivers SCS using those control parameters in an effort to trigger a parasympathetic response to alleviate the tachycardia. Electrodes positioned near one or more of the C7-T2 vertebra may be especially useful for delivering the neurostimulation. As another example, if bradycardia is instead detected, the device examines the mapping database to identify control settings associated with a sympathetic response (such as a relatively high LF and a relatively high LF/HF ratio) and then delivers further neurostimulation using that particular control setting to address the bradycardia. Electrodes positioned near the T5, T9-T10 and/or L1-L2 vertebra may be especially useful for delivering the neurostimulation (assuming the SCS lead includes electrodes positioned at one or more of those locations.)

In still other examples, if prolonged QT intervals are detected, the SCS device examines the mapping database to identify a set of control parameters associated with an appropriate response to prolonged QT and then delivers neurostimulation using the identified control settings to address the problem by, for example, working to reduce arrhythmia susceptibility within the patient. If the device is equipped with a contractility sensor for assessing the contractility of the heart, the device can examine the mapping database in response to a loss of contractility (often associated with progression of heart failure) to identify an appropriate control setting configuration for use in delivering further neurostimulation to address the reduced contractility. Similar techniques may be employed to address syncope, ischemia or myocardial infarction (as detected based on shifts in ST segments), acute pain (as detected based on a combination of elevated heart rate and patient movement associated with pain.) Within patients known to have coronary artery disease (CAD), the device may be programmed to deliver neurostimulation to preemptively address a possible ischemic insult. Still further, the device may be programmed to deliver neurostimulation to regularize PR intervals either as a prophylactic measure or in response to a detected tachycardia.

Thus, in various examples, cardiac signals are sensed by a SCS device and then neurostimulation is adjusted to address cardiovascular disorders or other conditions. As such, SCS programming may be tuned, in an automated manner, in dynamic response to the needs of heart failure and cardiac rhythm management. This is achieved without the need for a separate CRMD such as a pacemaker or implantable cardioverter-defibrillator (ICD). In addition to automatically adjusting neurostimulation, the SCS device can record suitable diagnostic information for subsequent clinician review and can generate alerts or warnings to alert the patient or caregiver, if warranted, such as in response to ischemia. Method and system examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of SCS System

Figure 1:
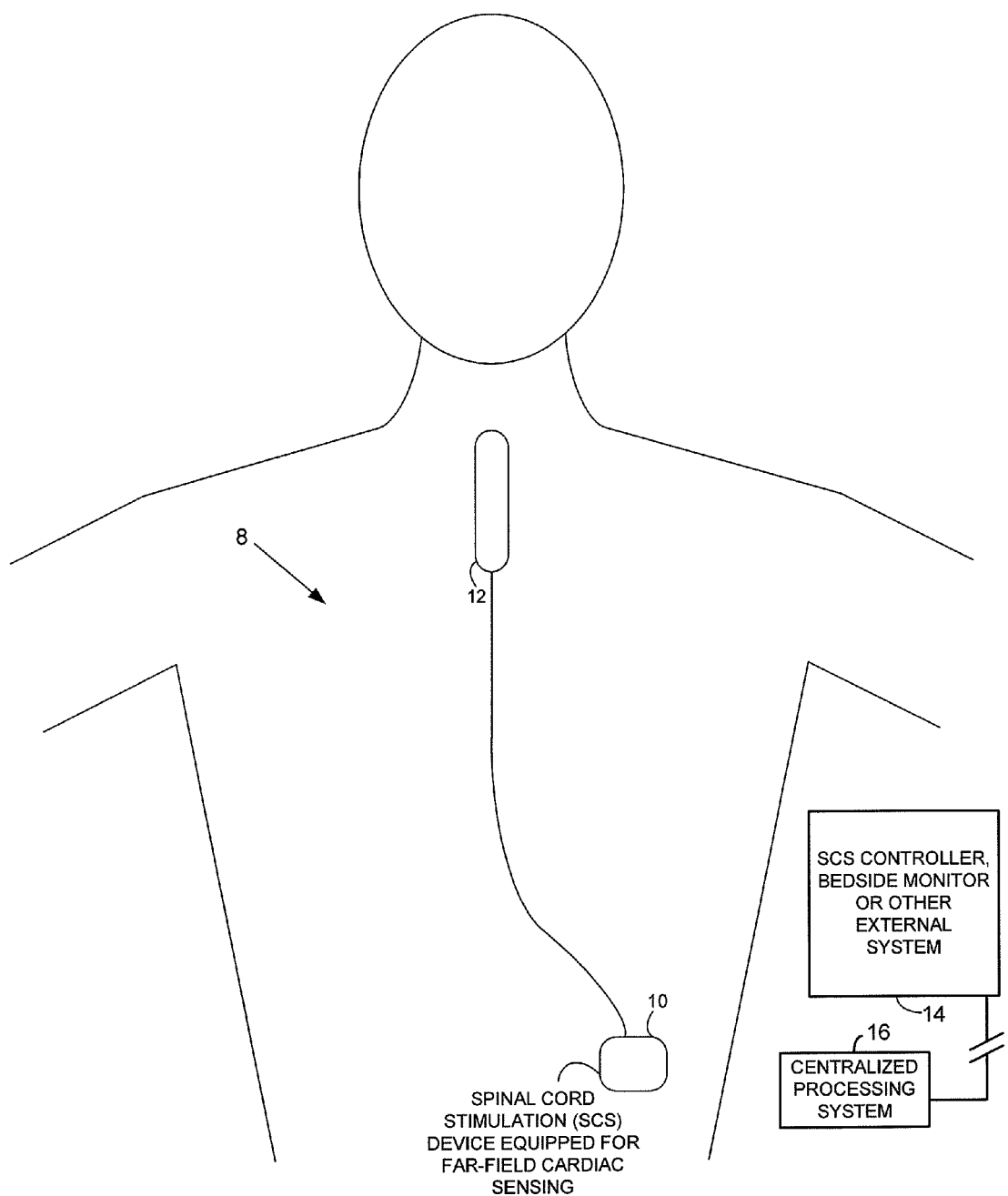
FIG. 1 illustrates pertinent components of an SCS system equipped to control neurostimulation based on far-field cardiac signals.

FIG. 1 illustrates an implantable medical system 8 having an SCS device 10 equipped to sense far-field electrical cardiac signals and to automatically adjust SCS control parameters to address cardiovascular disorders or other conditions detected based on the far-field signals. The far-field signals, which emanate from the heart of the patient (shown in FIG. 2), are sensed via an SCS lead or lead array 12 that is shown in FIG. 1 in stylized form. A more complete illustration of an exemplary SCS lead array and the positioning of its electrodes relative to the vertebra of the spine is provided in FIG. 2, described below. Note that the SCS device also delivers neurostimulation via lead 12 using a variety of combinations of neurostimulation control parameters (such as pulse frequency, amplitude, duration, vector, etc.) while (or after) far-field cardiac signals are sensed so as to allow the SCS device to map the effects of SCS to cardiac parameters. Data relating cardiac parameters to various combinations of neuromodulation control parameters is analyzed by the SCS device to identify combinations of neuromodulation control parameters that serve to address particular cardiovascular disorders.

Diagnostic data may then be transmitted to an external SCS programmer, bedside monitor or other system 14 such as personal advisory module (PAM). Additionally, warning signals or alerts pertaining to cardiovascular or other conditions can be transmitted to the external system to alert the patient or caregiver. The external system can forward warning signals or other information via a centralized processing system 16 to the patient's primary care physician or to others. The external system may include such systems as the HouseCall™ remote monitoring system or the Merlin@home system of St. Jude Medical. The centralized system may include the Merlin.Net system of St. Jude Medical. If equipped with an SCS controller, the external system 14 may allow the patient to transmit control signals directly to the implanted SCS device to override any neuromodulation control parameters set by the device itself, if needed to mitigate pain or for other reasons.

Although the example of FIG. 1 shows an SCS device, additional or alternative neurostimulation devices might be used such as devices for stimulating other nerves within the patient. Also, although the SCS devices described herein can sense far-field cardiac signals without the need for a separate CRMD, some patients might additionally have a CRMD. SCS devices can, where appropriate, be equipped to operate in conjunction with a CRMD.

Figure 2:
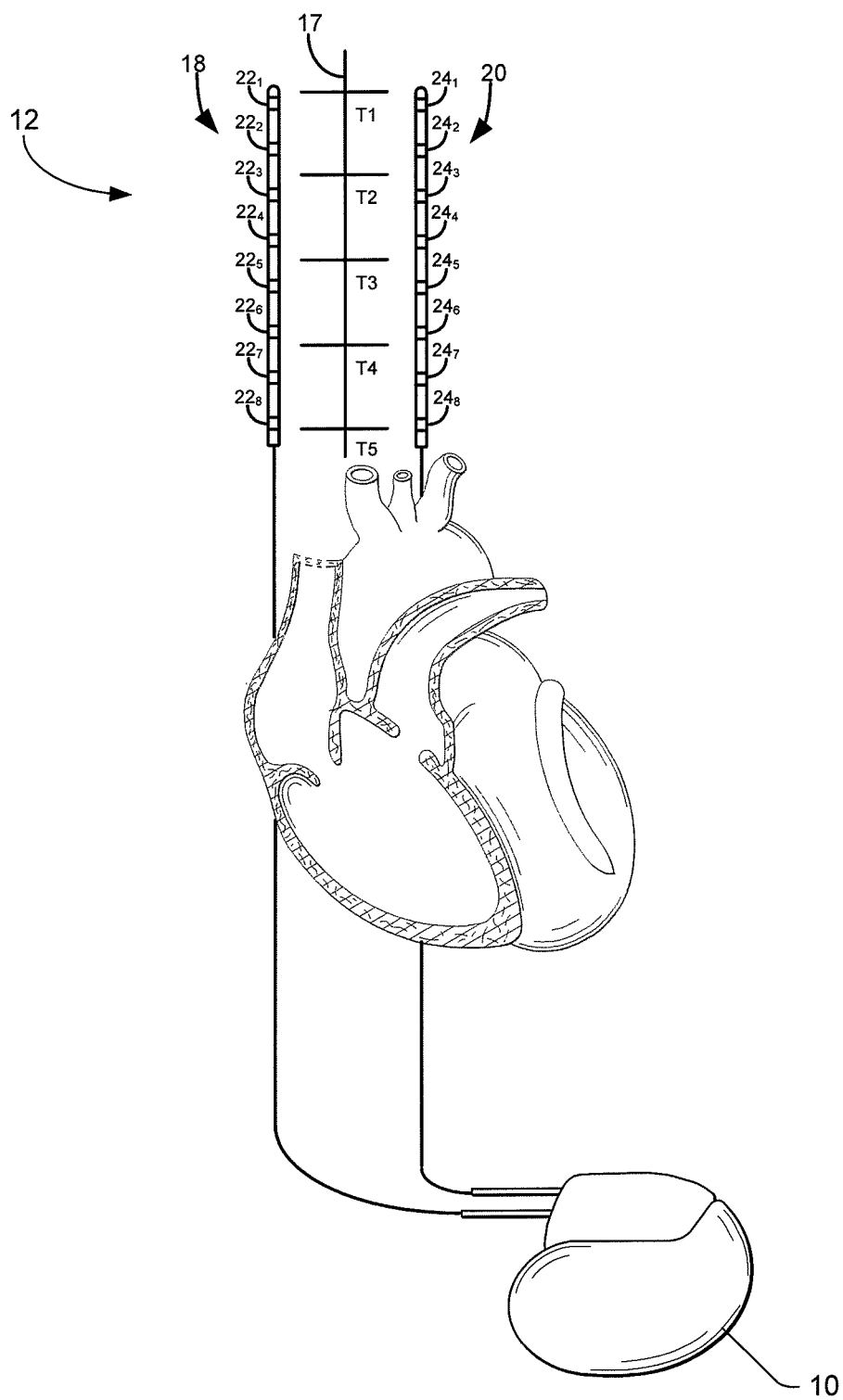
FIG. 2 illustrates exemplary implant locations for the SCS lead and SCS device of FIG. 1.

FIG. 2 illustrates an exemplary implementation where the SCS array 12 includes a pair of Octrode™ leads implanted along the upper spine. Octrode™ arrays are discussed, for example in, Alo et al., "Computer assisted and patient interactive programming of dual octrode spinal cord stimulation in the treatment of chronic pain" Neuromodulation. 1998; 1:30-45 and in Alo, "Lead positioning and programming strategies in the treatment of complex pain" Neuromodulation. 1999; 2:165-170.

In the example of FIG. 2, dual array 12 is implanted in the epidural space of the upper thoracic region adjacent the T1-T5 vertebra of the spine 17 (shown here in stylized form). That is, a first array 18 (having electrodes $22_1$-$22_8$) is implanted on one side of the spine and a second array 20 (having electrodes $24_1$-$24_8$) is implanted along the other side of the spine, with the distal-most of the electrodes of each array ($22_1$ and $24_1$, respectively) located above even with T1 and the proximal-most of the electrodes of each array ($22_8$ and $24_8$, respectively) located above even with T5. In this example, the SCS can is implanted in the abdomen. With this configuration, various sensing/stimulation vectors are can be exploited between individual electrodes of a particular array, between electrodes of opposing arrays, or between one or more electrodes of the arrays and the device can (housing) such as:

Electrode $22_1$-Electrode $24_8$
Electrode $22_1$-Can
Electrode $22_8$-Can

Moreover, stimulation using the electrodes of a particular array can be varied such as in accordance with the following exemplary options:

+ + + + − − − −
+ − + − + − + −
− − − − + + + + where a "+" indicates that the corresponding electrode of the selected array is used with positive polarity and a "−" indicates that the corresponding electrode of the selected array is used with a negative polarity. Still other examples are:

+ − 0 0 0 0 0 0
+ 0 0 0 0 0 0 −
+ + + + − − − −
+ 0 0 0 0 0 0 0 Can where the "0" indicates that the corresponding electrode is not used. Although these particular examples pertain to one array with eight selectable electrodes, it should be understood that the dual arrays could be controlled independently to provide additional stimulation configurations.

Note that in the example of FIG. 2, at least one (proximal) SCS electrode is implanted at about the same cranial-caudal (or cranial-posterior) level as the atria of the heart and at least one (distal) SCS electrode is implanted relatively farther from the cranial-caudal level of the atria. The housing (or can) of the SCS device is implanted at a location relatively remote from the SCS electrodes, such as in the abdomen. With this implant configuration, some sensing vectors pass relatively close to the atria; whereas others pass relatively farther from the atria, thereby providing different vectors emphasizing different features of the far-field cardiac signals, such as P-waves or R-waves. This can be exploited to aid in the discrimination of atrial and ventricular events, as will discussed in greater detail below. In other examples, the lead arrays may be implanted lower along the spine such that the distal electrodes are instead at substantially the same cranial-caudal level as the atria of the heart and the proximal electrodes are instead implanted relatively farther from the cranial-caudal level of the atria.

Note also that FIG. 2 provides a stylized illustration that does not necessarily set forth the precise location of the various anatomical features and implantable components, nor their relative sizes.

Exemplary SCS Systems and Methods

Figure 3:
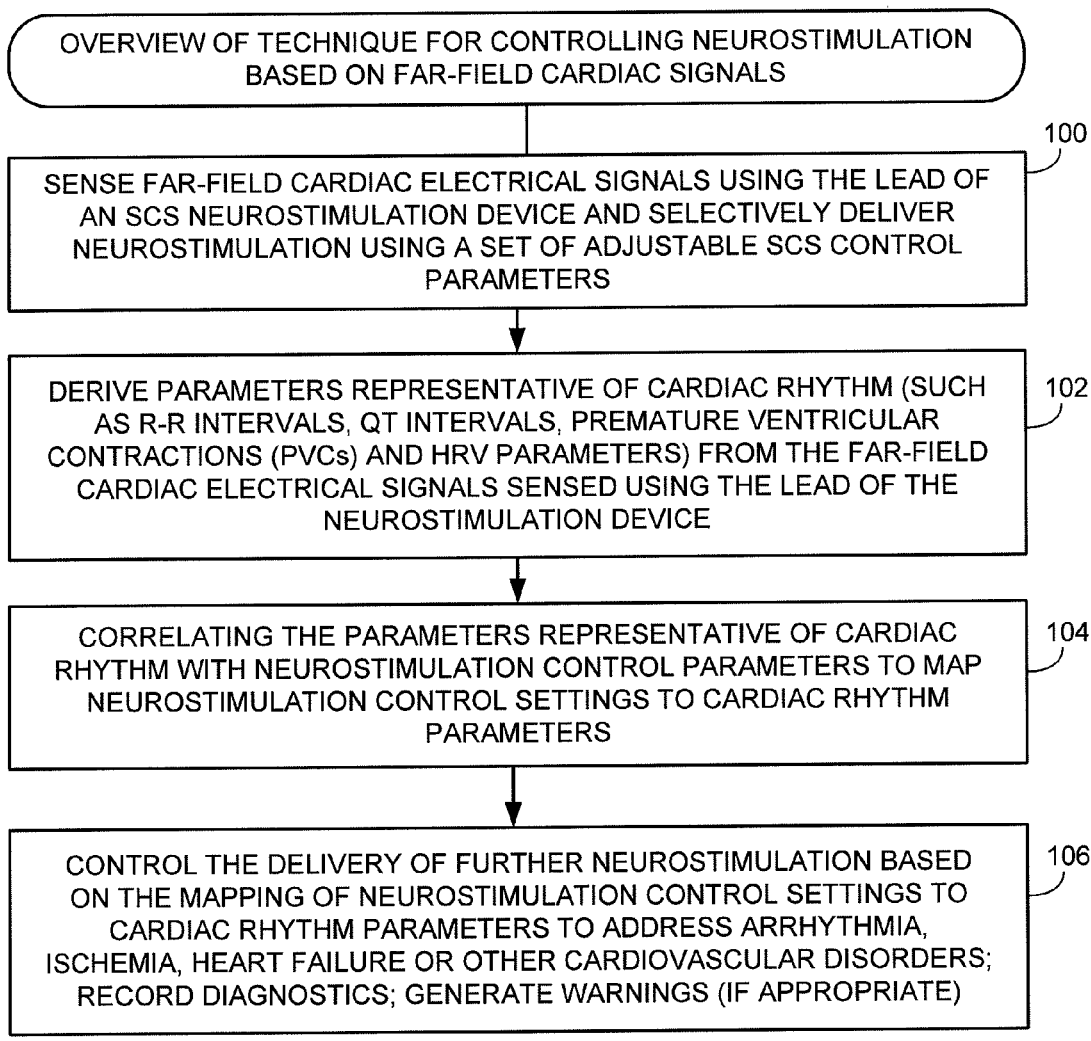
FIG. 3 is an overview of the method for controlling neurostimulation based on far-field cardiac signals performed by the system of FIG. 1.

FIG. 3 broadly summarizes neurostimulation control procedures implemented by the SCS system of FIG. 1 or other suitably-equipped implantable medical systems. Initially, at step 100, the SCS device senses far-field cardiac electrical signals using its SCS leads and selectively delivers neurostimulation using a set of adjustable SCS control parameters (such as pulse frequency, amplitude, duration, vector, etc.) At step 102, the device derives parameters representative of cardiac rhythm (such as QT interval duration, R-R interval durations, ST segment amplitude, premature ventricular contractions (PVCs) or HRV parameters) from the far-field cardiac electrical signals sensed using the leads of the neurostimulation device. At step 104, the device correlates the parameters representative of cardiac rhythm with neurostimulation control parameters to map neurostimulation control settings to the cardiac rhythm parameters. As will be explained, various tables may be generated that relate particular combinations of SCS control parameters to particular HRV parameters (or other parameters representative of cardiac rhythm) to thereby provide an atlas or library of information for guiding or tuning further adjustments to the SCS control parameters. At step 106, the SCS device controls the delivery of further neurostimulation based on the mapping of neurostimulation control settings to cardiac rhythm parameters to address arrhythmia, ischemia, heart failure or other disorders. The device may also record diagnostics and generate warnings, if appropriate. In particular, if the device tracks and stores R-R intervals, the SCS device thereby serves as an implantable loop recorder to provide diagnostic information to the clinician. Upon detection of tachycardia, bradycardia, syncope events, etc., an alert can be sent immediately to a physician or clinician via the remote connection.

Hence, a system and method is set forth that can sense R-waves independent of a cardiac pulse generator for providing closed-loop therapeutic procedures that sense cardiac electrical activity and use the detected R-waves as feedback diagnostics of arrhythmias and heart conditions to customize electrode configurations for neurostimulation. With the ability to sense R-waves, the SCS device can build a map/atlas/library of HRV parameters corresponding to different tested stimulation configurations. Depending on the sensed rhythm (bradycardia, tachycardia, etc), the SCS device then programs the appropriate stimulation configuration that will provide a parasympathetic or sympathetic increase/decrease according to the HRV atlas. In addition to providing continuous, closed-loop therapy for arrhythmias, the system may also monitor other disease conditions such as ischemia and acute pain and provide tailored stimulation.

Figure 4:
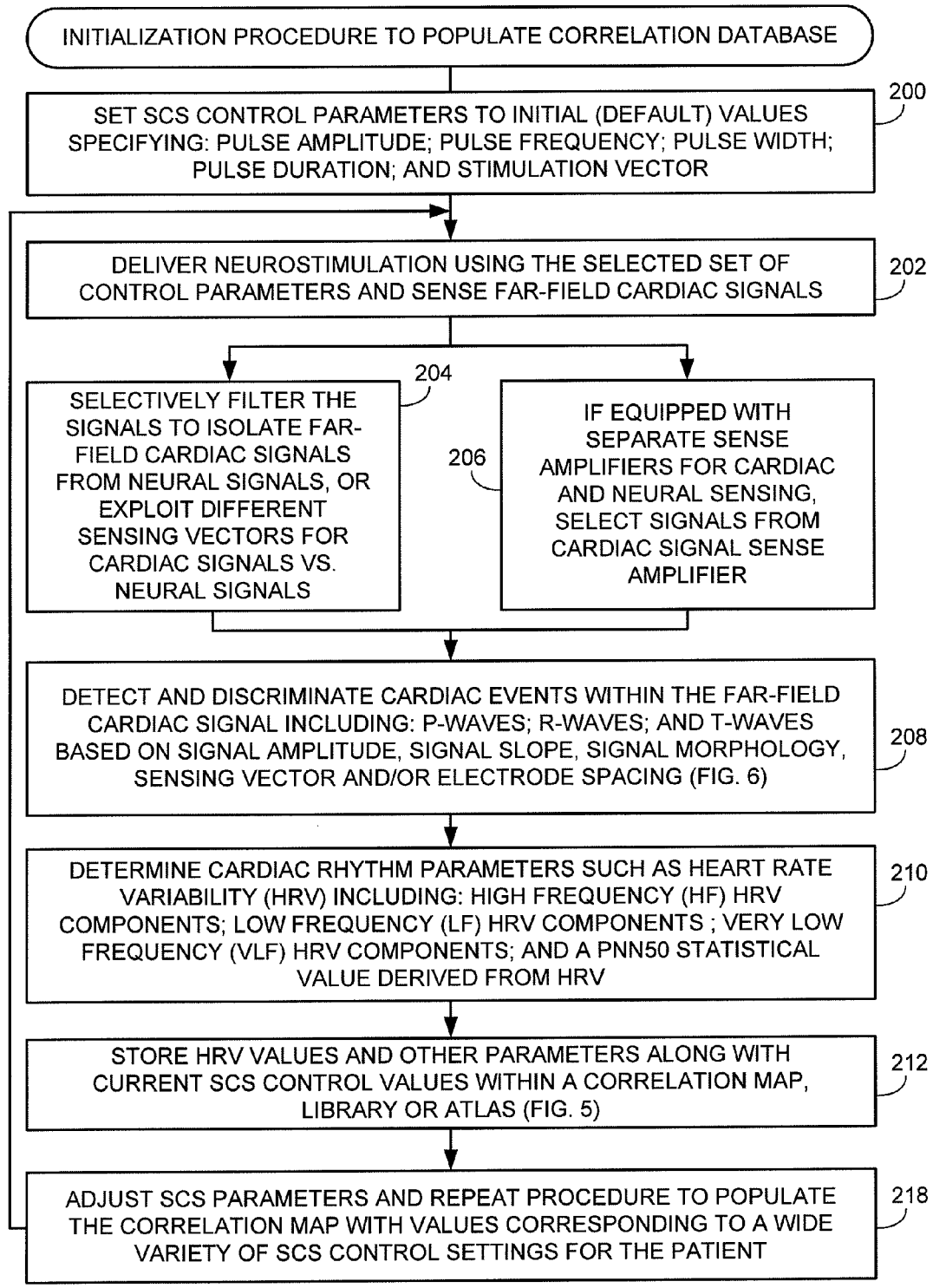
FIG. 4 illustrates an exemplary initialization procedure for populating mapping databases for use with the general technique of FIG. 3.

Turning now to FIG. 4, an exemplary initialization procedure will be described for use in populating the aforementioned correlation databases for an example where HRV is exploited. The initialization procedure may be performed post-implant and at certain follow-up visits. Beginning at step 200, SCS control parameters are set to initial (default) values specifying: pulse amplitude; pulse frequency; pulse width; pulse duration; and the stimulation vector (or vectors.) In one embodiment, the following ranges of values are programmable within the SCS device: pulse amplitude (0.1-5.5 mA); pulse frequency (2-500 Hz); pulse width (1-1000 μsec); and SCS duration (5 seconds to 15 minutes.) Hence, in one particular example, the initial values specified at step 200 within those programmable ranges might include: an initial 50% sub-threshold amplitude value (based on a previously-determined stimulation threshold); a 5 Hz value for pulse frequency; a 1 μsec value for pulse width and a five minute value for the SCS duration. The initial stimulation vector might be the vector between the most distal of the electrodes of the SCS lead and the most proximal electrode.

At step 202, neurostimulation is delivered by the SCS device using the selected set of control parameters and far-field cardiac electrical signals are sensed. Depending upon the particular implementation, SCS may be delivered first, with cardiac signals then sensed during an interval of time after SCS has been suspended, or the cardiac signals may be sensed while SCS is being delivered (assuming the ongoing SCS pulse trains do not interfere with the reliable sensing of far-field cardiac signals.) Note that, depending upon the particular sense amplifier configuration of the SCS, the device may need to filter a single wide band signal to extract the cardiac signals components, as indicated in step 204 or the device can exploit different sensing vectors for cardiac signals vs. neural signals. Alternatively, if equipped with separate sense amplifiers (one adapted for sensing neural electrical signals (e.g. 15 Hz to 2000 Hz to sense sympathetic neural activity (and more likely in the range of 14-40 Hz for near-field neural signals)), and the other adapted for sensing far-field cardiac signals (e.g. 20-60 Hz)), the SCS device can simply select the output of the cardiac signal sense amplifier to obtain the far-field cardiac signals. R waves are typically 25-40 Hz and T-waves are typically 3-10 Hz. (Note that the various frequency ranges listed herein are merely intended to be illustrative. Actual, preferred frequency ranges can be determined without undue experimentation.) In any case, once the SCS device has obtained the far-field cardiac signal (similar to a surface electrocardiogram (EKG) signal), the device at step 208 then detects and discriminates far-field cardiac rhythm events within the cardiac signal including: P-waves; R-waves; and T-waves based on signal amplitude, signal slope, signal morphology, sensing vector or sensing electrode spacing. This will be described in greater detail with reference to FIG. 6, below.

At step 210, the SCS device then determines cardiac rhythm parameters such as HRV including: HF, LF, LF/RF (i.e. the ratio of LV to HF) and VLF components of HRV; as well as a pNN50 statistical value derived from HRV (or other suitable pNNx values.) HF, LF and VLF components of HRV can be extracted or isolated using any suitable filtering techniques. HRV and its spectral components are discussed in: U.S. Patent Pub. No. 2011/0066055 to Bharmi et al., entitled "System and Method for use with an Implantable Medical Device for Detecting Stroke based on Physiological and Electrocardiac Indices" and in U.S. Pat. No. 7,711,415 to Farazi et al., entitled "Implantable Devices, and Methods for use Therewith, For Monitoring Sympathetic and Parasympathetic Influences on the Heart." See, also, the aforementioned patent application of Xi et al., cited above. Insofar as pNN50 is concerned, this statistical value is representative of the fraction of consecutive normal sinus (NN) intervals that differ by more than 50 ms and can be calculated using:

$$pNN50 = (NN50\ count)/(total\ NN\ count)$$

Other statistical values of the form pNNx might instead be used, where appropriate, where x>0 ms. For example, PNN50<3% could be used as a marker of low parasympathetic activity. At step 212, the SCS device stores the HRV values and other parameters along with current SCS control settings within a set of correlation databases that represent the aforementioned map, library or atlas.

Figure 5:
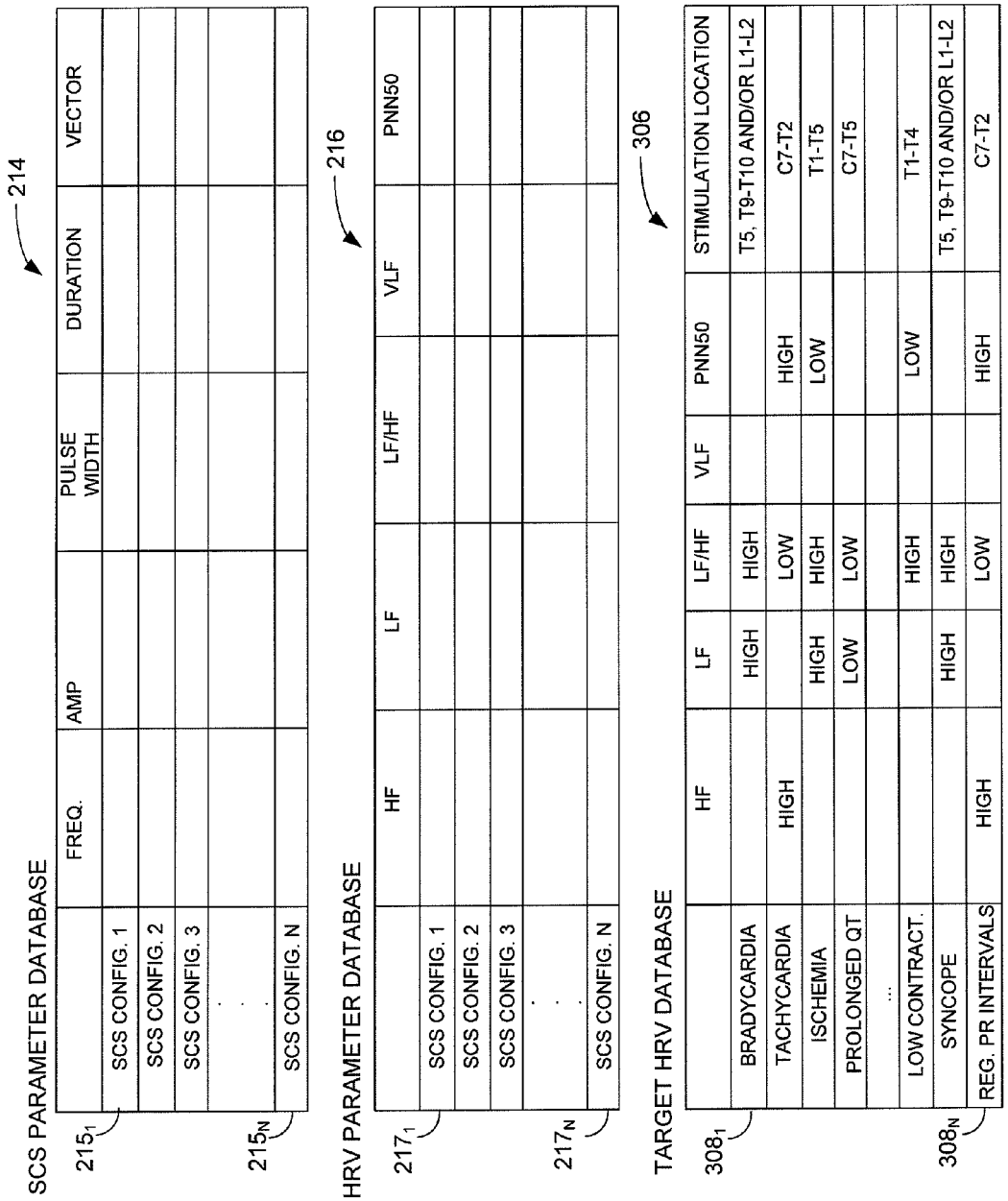
FIG. 5 illustrates tables/maps populated by the technique of FIG. 4 that relate SCS control parameters to corresponding HRV parameters assessed based on far-field cardiac signals, as well as illustrating a table indicating target HRV values to be achieved to address various cardiovascular conditions.

FIG. 5 illustrates an exemplary set of mapping databases. A first table or database 214 records different sets of SCS control parameters, i.e. different SCS configurations. For the first set of SCS parameters initially selected at step 200 of FIG. 4, the database stores the set as Configuration 1 (denoted $215_1$ in the figure.) A second database or table 216 stores the corresponding HRV values determined at step 210 of FIG. 4 for that particular SCS configuration within a first row of the table (denoted $217_1$.) The third database/table shown in FIG. 5 will be discussed below.

Returning to FIG. 4, at step 218, the SCS device then changes or adjusts its SCS parameters to specify a different SCS configuration and repeats the procedure of steps 202-212 to determine another set of HRV values for storing in the mapping databases of FIG. 5. For example, for the second SCS configuration, the SCS device may use the same stimulation vector but increase the pulse amplitude to 90% threshold, while holding constant the pulse frequency, pulse width, etc. In another iteration, the device might hold all other parameters besides pulse frequency constant, which is instead set to 50 Hz or 500 Hz. During some iterations of the procedure, the stimulation vector is changed (while other parameters are held constant) such as by selecting a different one of the exemplary stimulation configurations listed above. The procedure repeats until databases 214 and 216 of FIG. 5 are populated with values for at least several—and preferably many—different SCS configurations for the patient. In general, N configurations are tested to generate N rows of data in table 214 and N rows of data in table 216, with the last rows denoted $215_N$ and $217_N$, respectively. Once the mapping databases have been suitably populated, the SCS device can then use the data stored therein to guide SCS programming to address various cardiovascular conditions, as will be discussed below.

Further with regard to the use of HRV in FIG. 5: the HF power spectrum is evaluated in the range from 0.15 to 0.4 Hz. This band reflects parasympathetic (vagal) tone and fluctuations caused by spontaneous respiration known as respiratory sinus arrhythmia. The LF power spectrum is evaluated in the range from 0.04 to 0.15 Hz. This band can reflect both sympathetic and parasympathetic tone. The VLF power spectrum is evaluated in the range from 0.0033 to 0.04 Hz. The physiological meaning of this band is not entirely clear. With longer recordings it is considered representing sympathetic tone as well as slower humoral and thermoregulatory effects. There is some indication that in shorter recordings VLF has fair representation of various negative emotions, worries, rumination, etc. The TP (i.e. total power) is a net effect of all possible physiological mechanisms contributing in HR variability that can be detected in 5-min recordings. However sympathetic tone is considered as a primary contributor. The LF/HF Ratio is used to indicate balance between sympathetic and parasympathetic tone. A decrease in this score might indicate either an increase in parasympathetic or decrease in sympathetic tone. It should be considered together with absolute values of both LF and HF to determine what factor contributes in autonomic disbalance.

Figure 6:
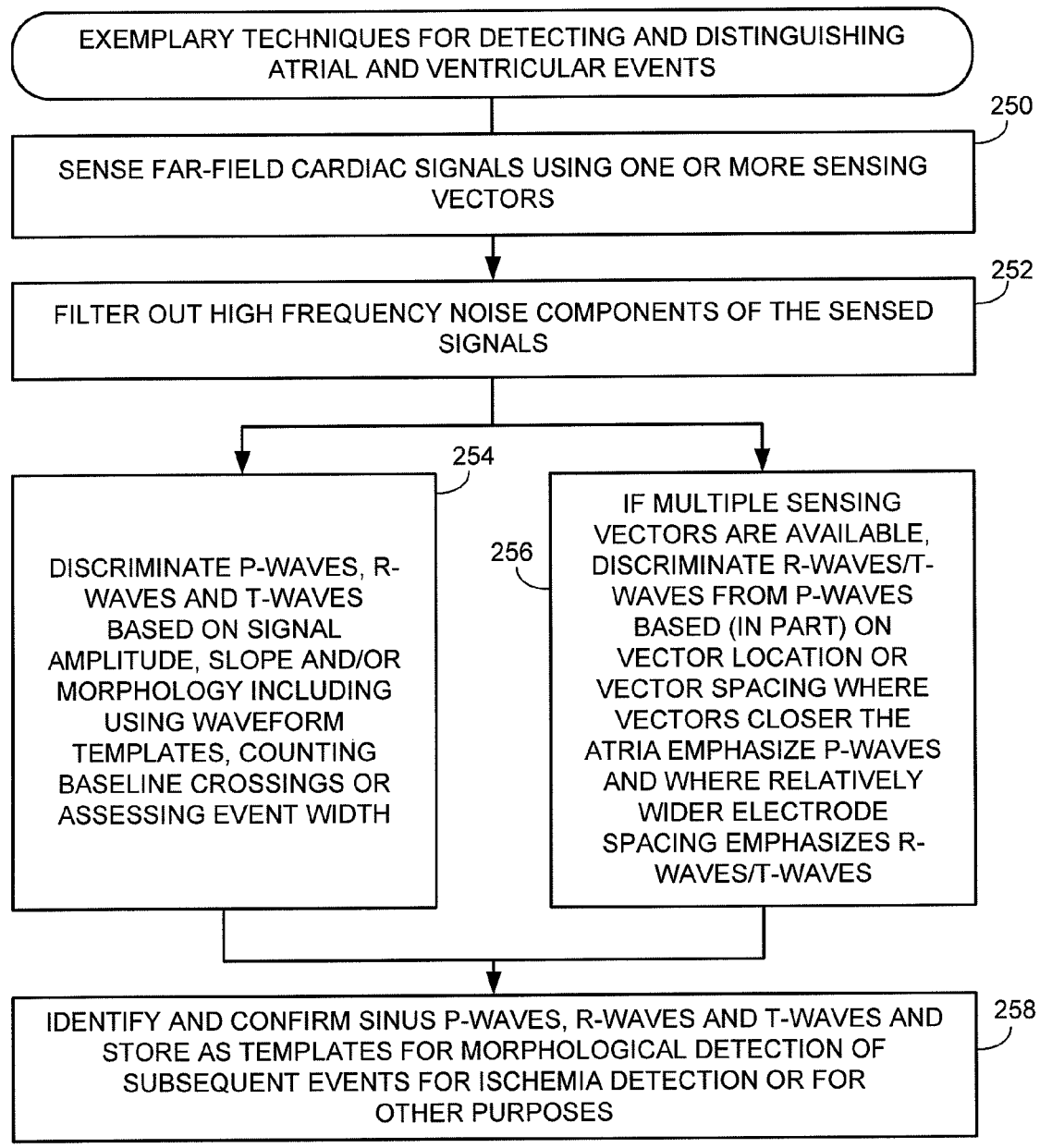
FIG. 6 illustrates an exemplary procedure for detecting and distinguishing atrial and ventricular events for use with the initialization procedure of FIG. 4 or at other times.

FIG. 6 illustrates techniques for detecting and discriminating atrial and ventricular events that may be used in conjunction with the initialization procedure of FIG. 4 or whenever atrial or ventricular events need to be detected. In general, reliable cardiac sensing involves discriminating "far field" (as measured from the spinal region) P-waves, R-waves and T-waves. This may be done for example based on amplitude: R waves are the tallest, and only those tallest waves are detected and used for monitoring purposes. Alternately, slope is used where a time derivative of the signal or a sharp high-pass filter is applied to identify R-waves, again used for monitoring. Morphology may be employed (e.g. correlation with template waveforms, counting the number of baseline crossings, the width of complexes, etc) in order to identify R, P and T waves which may all be used for monitoring and feedback. Still further, far-field cardiac signals measured from different spinal vectors may be used to identify atrial or ventricular activity, for example using one vector (that does not pass close to the atria) to identify all signals and pick R-waves by any of the above methods, and then further using (as a second channel) a different vector (that passes close to the atria) to selectively identify atrial activity. With any embodiments that allow distinction between R-waves and P-waves, not only R-R intervals but also other measures for SVT/VT discrimination (e.g. rate branch, integer ratios, AV dissociation, etc) may be detected and exploited.

In one particular discrimination example, beginning at step 250 of FIG. 6, the SCS device senses far-field cardiac signals using one or more sensing vectors and, at step 252, filters out high frequency noise components of the sensed signals, if needed. At step 254, the SCS device discriminates P-waves, R-waves and T-waves based on signal amplitude, slope and/or morphology, including using waveform templates, counting baseline crossings or assessing event width, as mentioned above. In examples where two or more sensing vectors are available (i.e. the SCS device has sufficient sense amplifiers and other components to process multiple input signal feeds), the SCS device at step 256 can additionally discriminate R-waves/T-waves from P-waves based on vector location or vector spacing where vectors closer the atria emphasize P-waves and relatively wider electrode spacing emphasizes R-waves/T-waves.

In this regard, since SCS electrodes are relatively distant to the heart, pseudo-EKG signals are sensed. With a cardiac sense amplifier, the sensing threshold is set higher than neural signals. To detect an R-wave instead of a P-wave, a pair of SCS electrodes with closer spacing can be selected for rejecting P-waves. At a sensed event, a detection window begins (similar to V-channels in pacemakers) and the peaks of R-waves are detected and confirmed as R-waves if the amplitude is greater than a pre-determined threshold. If R-wave is rejected, the device resumes searching for a new sensed event, and a new window is started at the next sensed event. Hence, the technique exploits the fact that a vector that is relatively close to the atria of the heart will more readily sense P-waves; whereas a vector relatively farther from the atria will typically not sense P-waves, but will sense R-waves and T-waves. Hence, information regarding the particular vector selected for sensing can be used to aid in the discrimination of far-field events.

Hence, using the techniques of steps 254 and 256 of FIG. 6, the SCS device detects and discriminates P-waves, R-waves and T-waves. These events are then exploited in the various exemplary techniques described herein to detect arrhythmia, ischemia, etc., and to determine HRV and related parameters. Additionally, at step 258, the device examines the events to identify and confirm sinus rhythm events (e.g. sinus P-waves, sinus R-waves and sinus T-waves), which it stores in memory as templates for morphological detection of subsequent events for ischemia detection or other purposes. In this regard, otherwise conventional techniques may be used for identifying and confirming sinus events, such as by examining heart rate, the durations of PR and QT intervals, etc., to detect and reject non-sinus events.

Turning now to the next set of figures, various techniques for detecting and responding to arrhythmias and other issues will now be described.

Figure 7:
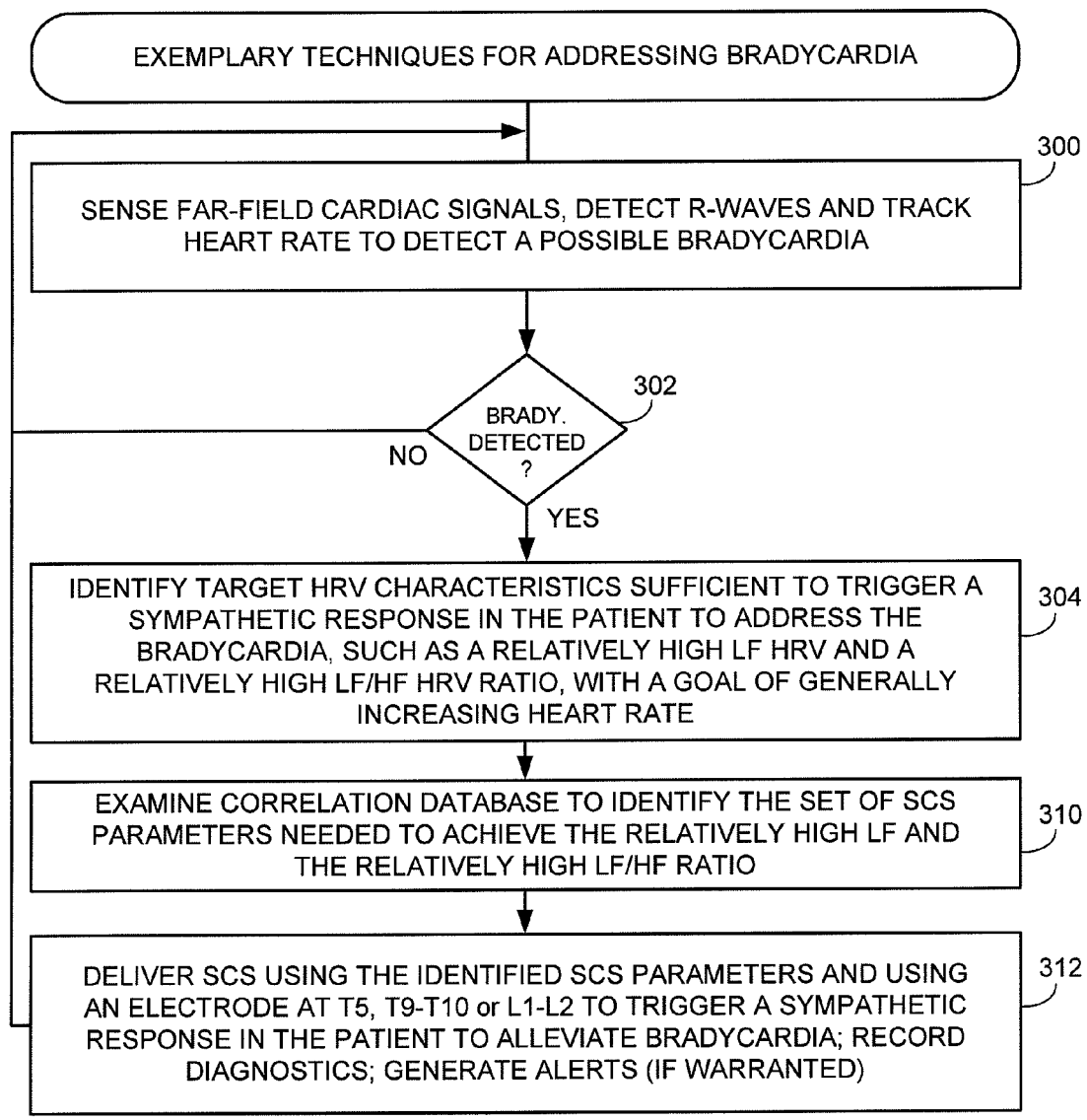
FIG. 7 illustrates an exemplary procedure for adjusting SCS in response to bradycardia for use with the general technique of FIG. 3.

FIG. 7 illustrates an example where the SCS device detects and responds to bradycardia. Beginning at step 300, the SCS device senses far-field cardiac signals, detects R-waves and tracks heart rate to detect a possible bradycardia (with bradycardia detected, for example, if the ventricular heart rate falls below a predetermined threshold value.) Assuming bradycardia is detected at step 302, the SCS device at step 304 identifies target HRV characteristics sufficient to trigger a sympathetic response in the patient to address the bradycardia with a goal of generally increasing heart rate, such as a relatively high LF HRV and a relatively high LF/HF HRV ratio. To this end, the device may store an additional database 306 (shown in FIG. 5), which provides predetermined target HRV values appropriate for bradycardia, as well as a preferred set of stimulation locations or vectors. For bradycardia, for example, the corresponding entry $308_1$ in the target HRV database specifies a relatively high value for LF and a relatively high value for the LF/HF ratio and indicates that the stimulation should be delivered at T5, T9-T10 and/or L1-L2. Hence, to identify the target HRV characteristics for use with bradycardia and the preferred stimulation locations, the device simply looks up the corresponding values in database 306. As another example, for prolonged QT, the corresponding entry in the target HRV database specifies a relatively low value for LF and a relatively low value for the LF/HF ratio and indicates that the stimulation should be delivered at C7-T5. (Note that it does not presently appear possible to modulate QT directly by SCS since QT prolongation might be due to the substrate, electrolyte imbalance or long standing diabetes. However, the SCS device can, and preferably should, deliver SCS stimulation to reduce arrhythmia susceptibility in these patients.) As yet another example, for syncope, the corresponding entry in the target HRV database specifies a relatively high value for LF and a relatively high value for the LF/HF ratio and indicates that the stimulation should be delivered at T5, T9-T10 and/or L1/L2. The goal of the SCS stimulation is to provide immediate and temporary support during a syncopal episode. In some examples, actual numerical values might be stored within the database for the various HRV entries. In other cases, as shown, the database instead just indicates whether certain HRV values should be relatively high or low. In any case, the various entries in the database may be preprogrammed by the clinician or otherwise set in advance. Note also that while some specific cardiovascular conditions are listed in table 306 such as bradycardia, low contractility and syncope, it should be understood that the table may list more or fewer conditions and/or may further specify certain conditions such as by further distinguishing among various types of tachycardia: atrial tachycardia, ventricular tachycardia, etc.

At step 310 of FIG. 7, the SCS device then examines the mapping databases (tables 214 and 216 of FIG. 5) to identify the set of SCS parameters needed to achieve the relatively high LF and the relatively high LF/HF ratio specified for use with bradycardia. That is, the SCS device searches database 216 to identify an SCS configuration (if any) that achieved those values during the initialization procedure. In an example where Configuration 3 achieved the appropriate HRV values, the SCS device then looks up the SCS control parameters that correspond to that configuration (i.e. Configuration 3) from database 214. At step 312 of FIG. 7, the SCS device then delivers SCS pulse trains using the identified SCS parameters and the appropriate stimulation configuration. For bradycardia, stimulation may thereby be delivered using one or more electrodes at T5, T9-T10 and/or L1-L2 to trigger a sympathetic response in the patient to address the bradycardia. Also, at step 312, the SCS records suitable diagnostics (e.g. heart rate, time of day, etc.) and generates warnings or alerts (if warranted) to notify the patient or clinician.

In this manner, the mapping databases are used to identify a set of SCS control parameters for responding to bradycardia within the patient. It should be noted that the particular SCS parameters appropriate for one patient might be different from those of other patients and so the procedure allows the preferred or optimal SCS parameters to be tailored or adapted to individual patients. Note also that, if none of the entries in database 216 of FIG. 5 achieves the target HRV values specified for use with bradycardia, then suitable warnings can be generated to advise the clinician.

Figure 8:
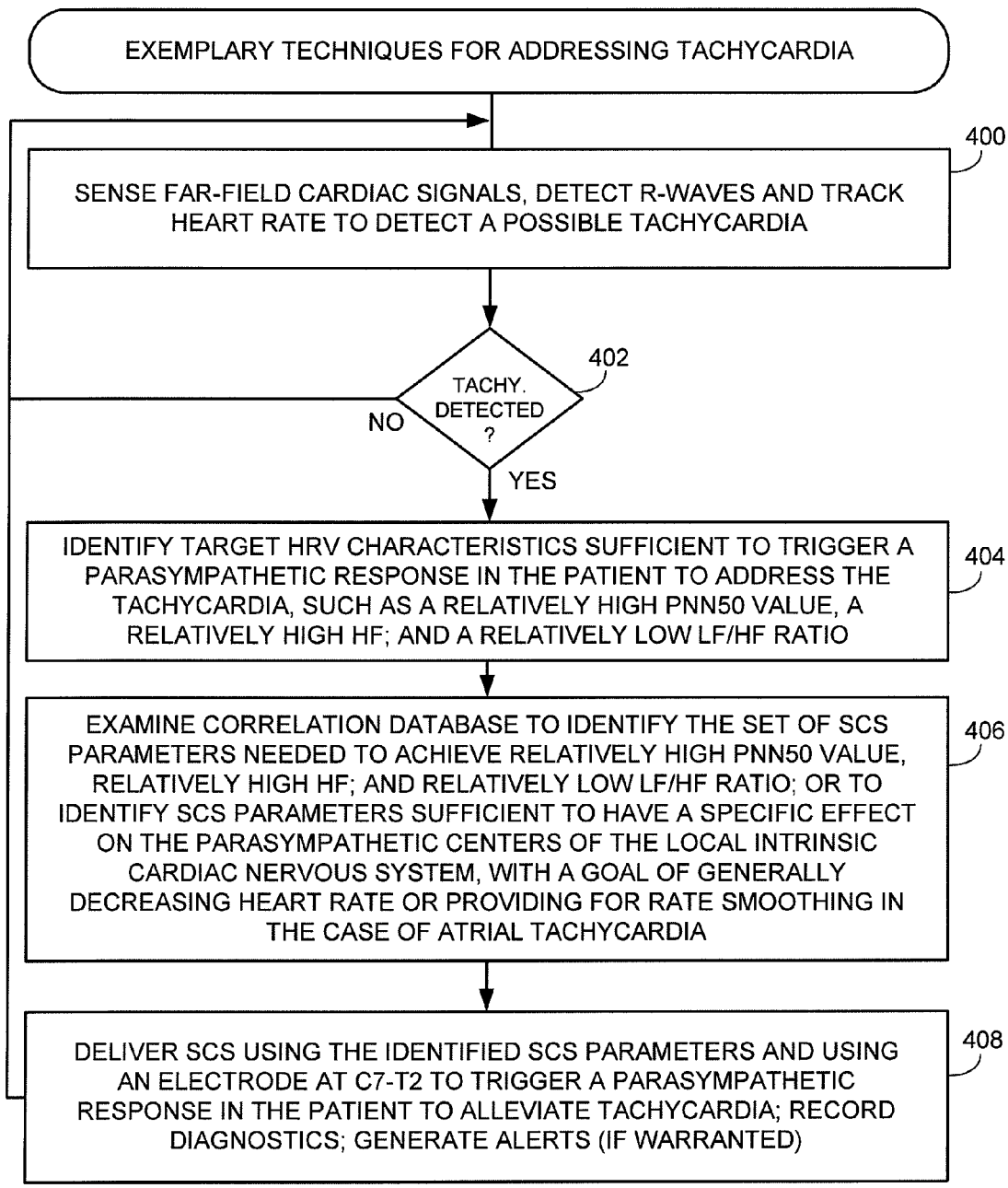
FIG. 8 illustrates an exemplary procedure for adjusting SCS in response to tachycardia for use with the general technique of FIG. 3.

FIG. 8 illustrates an example where the SCS device instead responds to tachycardia with a goal of generally decreasing heart rate or providing for rate smoothing in the case of atrial tachycardia. Many of the steps are similar to those of FIG. 6 and hence will not be described again in detail. Briefly, beginning at step 400, the SCS device senses far-field cardiac signals to detect a possible tachycardia (with tachycardia detected, for example, if the ventricular heart rate exceeds a predetermined threshold value.) Assuming tachycardia is detected at step 402, the SCS device at step 404 identifies target HRV characteristics sufficient to trigger a parasympathetic response in the patient to address the tachycardia, such as a relatively high pNN50 value, a relatively high HF; and a relatively low LF/HF ratio. The target HRV values may be obtained from database 306 of FIG. 5, which also indicates the preferred set of stimulation locations or vectors, in this case the C7-T2 locations. (See, Liu et al., J Cardiovasc Electrophysiol. 2012 May; 23(5):534-40. "Thoracic spinal cord stimulation improves cardiac contractile function and myocardial oxygen consumption in a porcine model of ischemic heart failure.") At step 406 of FIG. 8, the SCS device then examines the mapping databases of FIG. 5 to identify the set of SCS parameters needed to achieve the relatively high pNN50 value, relatively high HF; and the relatively low LF/HF ratio, or to identify SCS parameters sufficient to have a specific effect on the parasympathetic centers of the local intrinsic cardiac nervous system. In this regard, note that the intrinsic cardiac nervous system is the set of nerves and ganglia distributed over the cardiac anatomy. (See, generally, Pauza et. al., Cells Tissues Organs 2002, Vol. 172, No. 4. "Morphology of the Intrinsic Cardiac Nervous System in the Dog: A Whole-Mount Study Employing Histochemical Staining with Acetylcholinesterase.")

In an example where Configuration 7 achieved the appropriate HRV values during the initialization procedure (or had the specific desired effect on the parasympathetic centers of the local cardiac nervous system), the SCS device then looks up SCS control parameters that correspond to that configuration from database 214. At step 408 of FIG. 8, the SCS device delivers SCS using an electrode at C7-T2 to trigger a parasympathetic response in the patient to address tachycardia, records diagnostics, generates alerts (if warranted), etc. If none of the entries in database 216 of FIG. 5 achieves the target HRV values specified for tachycardia, suitable warnings can be generated to advise the clinician. Note that, for tachycardia therapy, regularization of the PR interval may be a complementary target. (Regularization of PR intervals is discussed below with reference to FIG. 13.)

Figure 9:
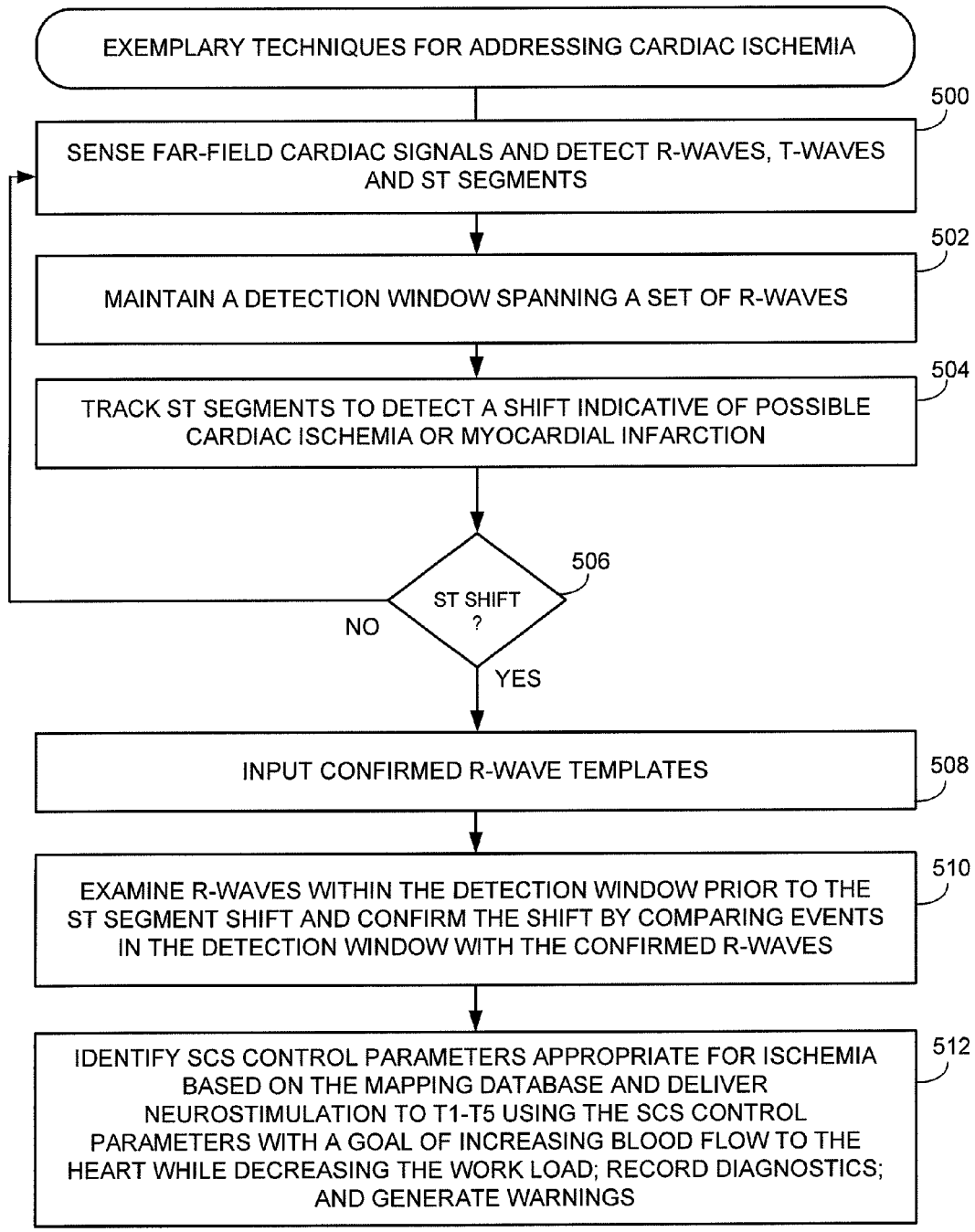
FIG. 9 illustrates an exemplary procedure for adjusting SCS in response to cardiac ischemia for use with the general technique of FIG. 3.

FIG. 9 illustrates an example where the SCS device detects and responds to cardiac ischemia with a goal of increasing blood flow to the heart while decreasing the work load. With an increase in sympathetic tone, the blood flow to the vital organs is improved, i.e. heart, brain. This is especially true to patients with silent ischemia in whom the system does not react to the ischemic event. In this case, and ST procedure/algorithm of the device would pick up the ischemia and the SCS would correctly react to it. Again, many of the steps are similar to those already described and hence will not be described again in detail. Beginning at step 500, the SCS device senses far-field cardiac signals and detects R-waves, T-waves and ST segments (i.e. the interval from the end of the QRS complex associated with the R-wave to the beginning of the subsequent T-wave.) As the SCS device detects these events, the device at step 502 maintains a detection window spanning a set of R-waves (such as the last minute or two worth of R-waves.) The detection window will be used to help confirm ischemia. At step 504, the device tracks the ST segments to detect an elevation shift indicative of possible ischemia or myocardial infarction. Techniques for detecting cardiac ischemia using on ST intervals or other suitable parameters (derived from cardiac signals sensed by a CRMD)

are discussed, for example, in U.S. Pat. No. 6,108,577 to Benser, entitled "Method and Apparatus for Detecting Changes in Electrocardiogram Signals" and U.S. Pat. No. 7,225,015, entitled "System and Method for Detecting Cardiac Ischemia Based on T-Waves Using an Implantable Medical Device" to Min et al. Although the technique of FIG. 9 instead exploits far-field cardiac signals sensed using the SCS device rather than signals sensed using a CRMD, the principles of ST-based ischemia detection described in the cited patents are nevertheless applicable.

Assuming that an ST shift is detected at step 506 (indicative of a possible ischemia), the SCS device then inputs confirmed R-wave templates such as those stored at step 258 of FIG. 6. At step 510, the device examines R-waves within the detection window prior to the ST segment shift and confirms the shift by comparing events in the detection window with the confirmed R-waves. For example, morphological features of the R-waves in the detection window may be compared against a template representative of a confirmed sinus R-waves to confirm that the events in the detection window are indeed true sinus R-waves. Assuming the events in the detection window are true sinus R-waves, then the ST shift is confirmed as a true ST shift and cardiac ischemia is thereby indicated. (If not, the ST shift is disconfirmed and processing can return to step 500 to sense additional far-field cardiac signals so that the detection procedure can be repeated with newly detected signals.)

At step 512, the device then identifies the SCS control parameters appropriate for ischemia based on the mapping database and delivers neurostimulation using those SCS control parameters, records diagnostics, generates alerts (if warranted). As with the bradycardia and tachycardia examples, target HRV values may be obtained from database 306 of FIG. 5, which may also indicate the preferred set of stimulation locations or vectors for use with ischemia. For ischemia, an exemplary set of target HRV parameters to be achieved within the patient using SCS to help alleviate the ischemia includes achieving a relatively high LF, a relatively low LF/HF ratio and a relatively low PNN50 by applying stimulation to T1-T5 to increase blood flow to the heart while decreasing the work load. Using those target HRV values, the SCS device then examines database 216 to identify the particular SCS configuration appropriate for achieving those target values and then consults database 214 to determine the particular SCS control parameters to be used. If none of the entries in database 216 of FIG. 5 achieves the target HRV values specified for ischemia, suitable warnings can be generated to advise the clinician.

Figure 10:
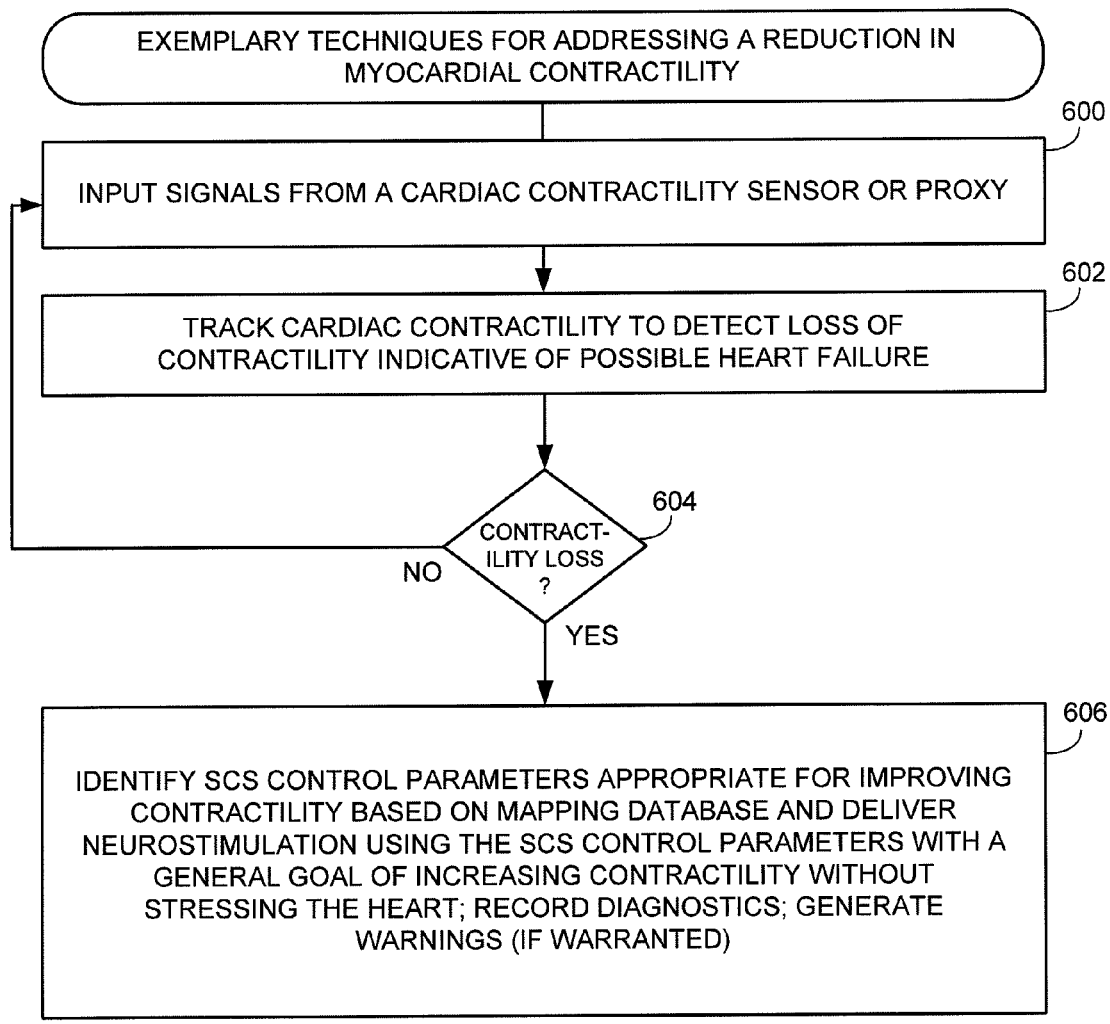
FIG. 10 illustrates an exemplary procedure for adjusting SCS in response to contractility changes for use with the general technique of FIG. 3.

FIG. 10 illustrates an example where the SCS device responds to changes in cardiac contractility (i.e. the contractility of heart muscle, particularly in the ventricles) as detected using a separate cardiac contractility sensor. Beginning at step 600, the SCS device inputs signals from a cardiac contractility sensor or proxy and, at step 602, tracks cardiac contractility to detect loss of contractility indicative of the possible onset or progression of heart failure. See, U.S. Patent Application 2011/0125208 of Karst et al. entitled "Methods and Systems to Monitor Cardiac Contractility." Contractility sensors are also discussed, for example, in U.S. Patent Pub. No. 2011/0224555 of Park, entitled "Systems and Methods for Use By an Implantable Medical Device for Detecting and Discriminating Stroke and Cardiac Ischemia Using Electrocardiac Signals and Hemodynamic Parameters"; U.S. Pat. No. 7,908,004 to Gill et al., entitled "Considering Cardiac Ischemia in Electrode Selection"; and in U.S. Pat. No. 6,788,970 to Park et al., entitled "System and Method for Treating Vasovagal Syncope using Cardiac Pacing." In at least some of these documents, contractility sensing is described in conjunction with CRMDs but the techniques may be applicable for use with a suitably-equipped standalone SCS device as well.

Assuming that a significant drop in cardiac contractility is detected at step 604 (indicative of possible onset or progression of heart failure), the SCS device at step 606 then identifies the SCS control parameters appropriate for improving contractility based on the mapping database with a general goal of increasing contractility without stressing the heart and delivers neurostimulation using those SCS control parameters, records diagnostics, and generates alerts (if warranted). (See, again, Liu et al., which indicates that SCS can result in an increase in contractility.) As with the examples above, target HRV values may be obtained from database 306 of FIG. 5, which may also indicate the preferred set of stimulation locations or vectors for improving contractility. An exemplary set of target HRV parameters to be achieved within the patient using SCS to help remedy the loss of contractility includes a relatively high LF/HF ratio and a relatively low PNN50. Using those target HRV values, the SCS device then examines database 216 to identify the particular SCS configuration appropriate for achieving those target values (T1-T4) and then consults database 214 to determine the particular SCS control parameters to be used. As with the above examples, if none of the entries in database 216 achieves the target HRV values specified for use in response to a drop in contractility, suitable warnings can be generated to advise the clinician.

Figure 11:
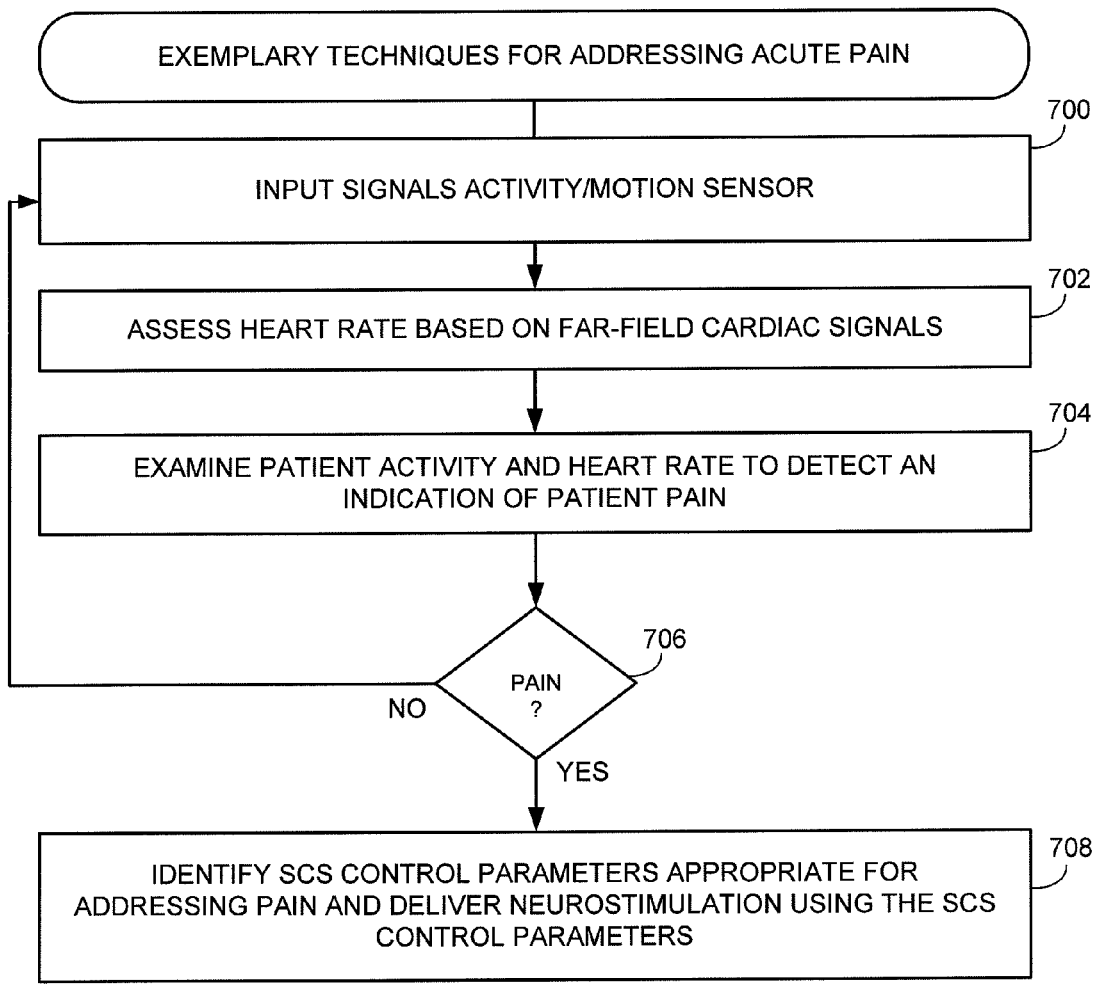
FIG. 11 illustrates an exemplary procedure for adjusting SCS in response to pain for use with the general technique of FIG. 3.

FIG. 11 illustrates an example where the SCS device responds to acute patient pain as detected based on heart rate and patient activity/motion. Beginning at step 700, the SCS device inputs signals from an activity/motion sensor or proxy and, at step 702, assesses heart rate based on far-field cardiac signals. In general, certain patient movements, accompanied by an increase in heart rate, may be indicative of acute pain exacerbation, which triggers the movement. In particular, certain patient movements may be associated with certain kinds of pain, such lower back pain, and a sensor equipped to monitor postural changes in the patient may be used to detect those pain-related movements. Opposing movements with a reduction in heart rate may be indicative of pain relief. Techniques for tracking changes in patient posture are described in U.S. Pat. No. 7,149,584 to Koh et al., entitled "System and Method for Determining Patient Posture based on 3-D Trajectory using an Implantable Medical Device." Activity sensors are also discussed, for example, in U.S. Pat. No. 7,123,967 to Weinberg, entitled "Implantable Neural Stimulation Device providing Activity, Rest, and Long Term Closed-Loop Peripheral Vascular Disease Therapy and Method" and in U.S. Pat. No. 6,002,963 to Mouchawar et al., entitled "Multi-axial Accelerometer-Based Sensor for an Implantable Medical Device and Method of Measuring Motion Measurements Therefor." In at least some of these documents, activity and motion sensors are described in conjunction with CRMDs but similar sensors can be exploited using a suitably-equipped standalone SCS device instead. Techniques for assessing pain based on physiological signals and parameters are discussed, for example, in U.S. Pat. No. 7,407,485 to Huiku, entitled "Monitoring Pain-related Responses of a Patient." Posture detection (in conjunction with heart rate monitoring) may also be used to detect syncope, particularly if the syncope arises as a result of an abrupt change in posture.

Assuming that acute pain is detected at step 706, the SCS device at step 708 then identifies the SCS control parameters appropriate for addressing the pain and delivers neurostimulation using those SCS control parameters, records diagnostics, generates alerts (if warranted). In contrast to the examples described above, the SCS device need not access the databases of FIG. 5 that relates HRV to SCS, as pain mitigation is not necessarily correlated with HRV. Rather, the SCS consults other databases to determine the appropriate SCS control parameters for use in mitigating pain. See, for example, the systems and techniques described in: U.S. patent application Ser. No. 13/442,749 of Xi et al., cited above.

Figure 12:
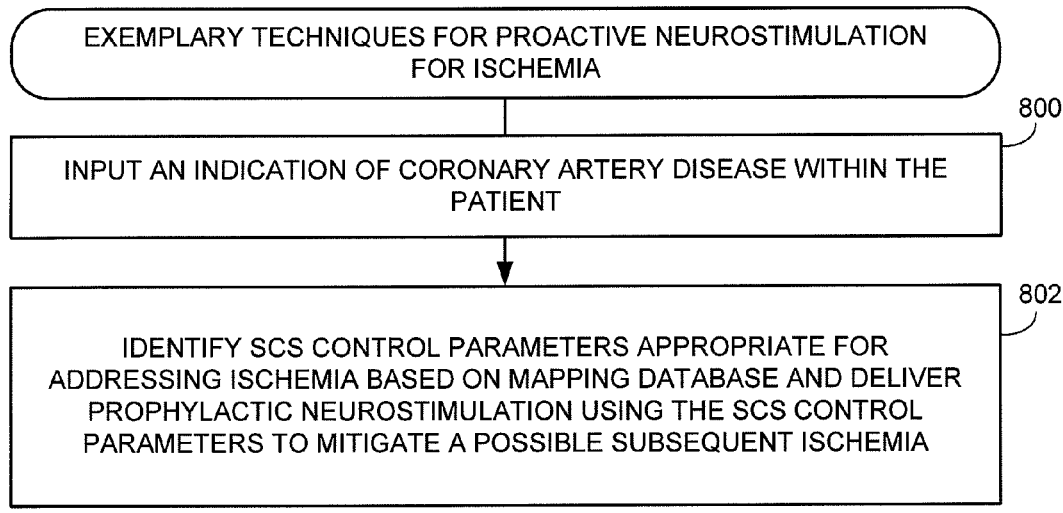
FIG. 12 illustrates an exemplary procedure for adjusting SCS to provide proactive neurostimulation in CAD patients for use with the general technique of FIG. 3.
Figure 13:
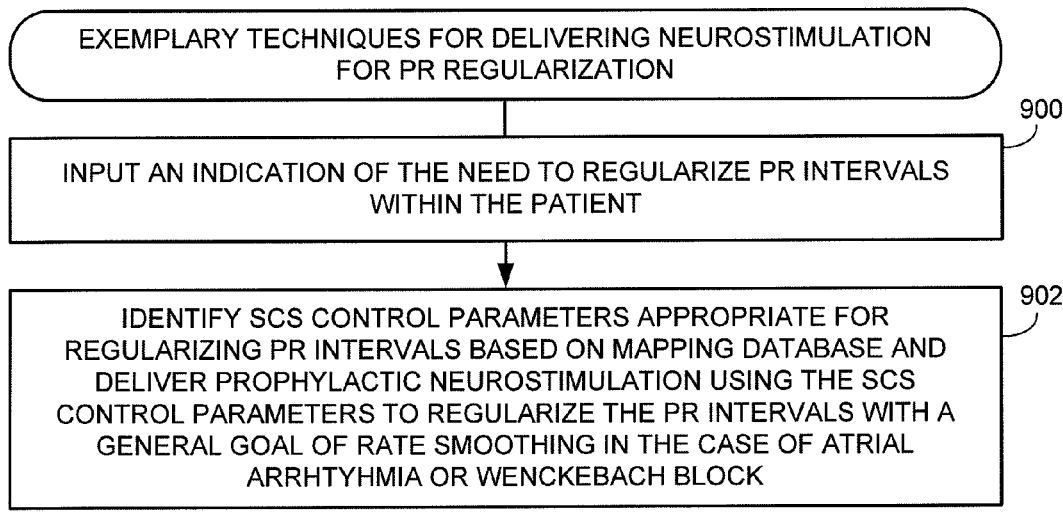
FIG. 13 illustrates an exemplary procedure for adjusting SCS to provide proactive neurostimulation to regularize PR intervals for use with the general technique of FIG. 3.

Thus, various exemplary techniques have been described with reference to FIGS. 7-11 for detecting and responding to certain conditions within the patient. Additionally, or alternatively, the SCS device can perform proactive or prophylactic procedures to mitigate particular conditions within patients at risk for those conditions. FIGS. 12 and 13 set forth two examples.

FIG. 12 briefly summarizes a technique for proactive neurostimulation for ischemia. At step 800, the SCS device inputs an indication of coronary artery disease (CAD) within the patient. For example, this determination may be made by a clinician, then programmed into the device during an initial SCS programming session. At step 802, the device then identifies SCS control parameters appropriate for addressing ischemia based on the mapping databases of FIG. 5 and delivers prophylactic neurostimulation using the SCS control parameters to mitigate possible subsequent ischemic insults. To this end, the SCS therapy would confer a protective benefit by causing peripheral vasoconstriction and constriction of renal arteries. Exemplary target HRV parameters to be achieved within the patient using SCS for ischemia are discussed above with reference to FIG. 9. Using those target HRV values, the SCS device examines database 216 of FIG. 5 to identify the particular SCS configuration appropriate for achieving those target values and then consults database 214 to determine the particular SCS control parameters to be used. SCS is then delivered prophylactically using the determined SCS control parameters in an effort to mitigate a possible ischemic insult that might arise within the patient.

FIG. 13 briefly summarizes a technique for regularizing PR intervals. As either a preventative anti-arrhythmic therapy or in response to detection of arrhythmia, the SCS device at step 900 inputs an indication of the need to regularize PR intervals within the patient. This determination may be made by a clinician then programmed into the device during an initial SCS programming session (or may be made based on detection of tachycardia.) At step 902, the device then identifies SCS control parameters appropriate for regularizing PR intervals based on the mapping databases of FIG. 5 and delivers prophylactic neurostimulation using the SCS control parameters to regularizing PR intervals. Exemplary target HRV parameters to be achieved within the patient using SCS to help regularize PR intervals include a relatively high HF, relatively low LF/HF and relatively high PNN50 with stimulation delivered at C7-T2 with a goal of rate smoothing in the case of arrhythmia or Wenckebach block. Using those target HRV values, the SCS device examines database 216 of FIG. 5 to identify the particular SCS configuration appropriate for achieving those target values and then consults database 214 to determine the particular SCS control parameters to be used. SCS is then delivered using the determined SCS control parameters in an effort to regularizing PR intervals within the patient to obtain the benefits thereof, either as a proactive measure or as a reactive anti-arrhythmic therapy such as in response to tachycardia.

Figure 14:
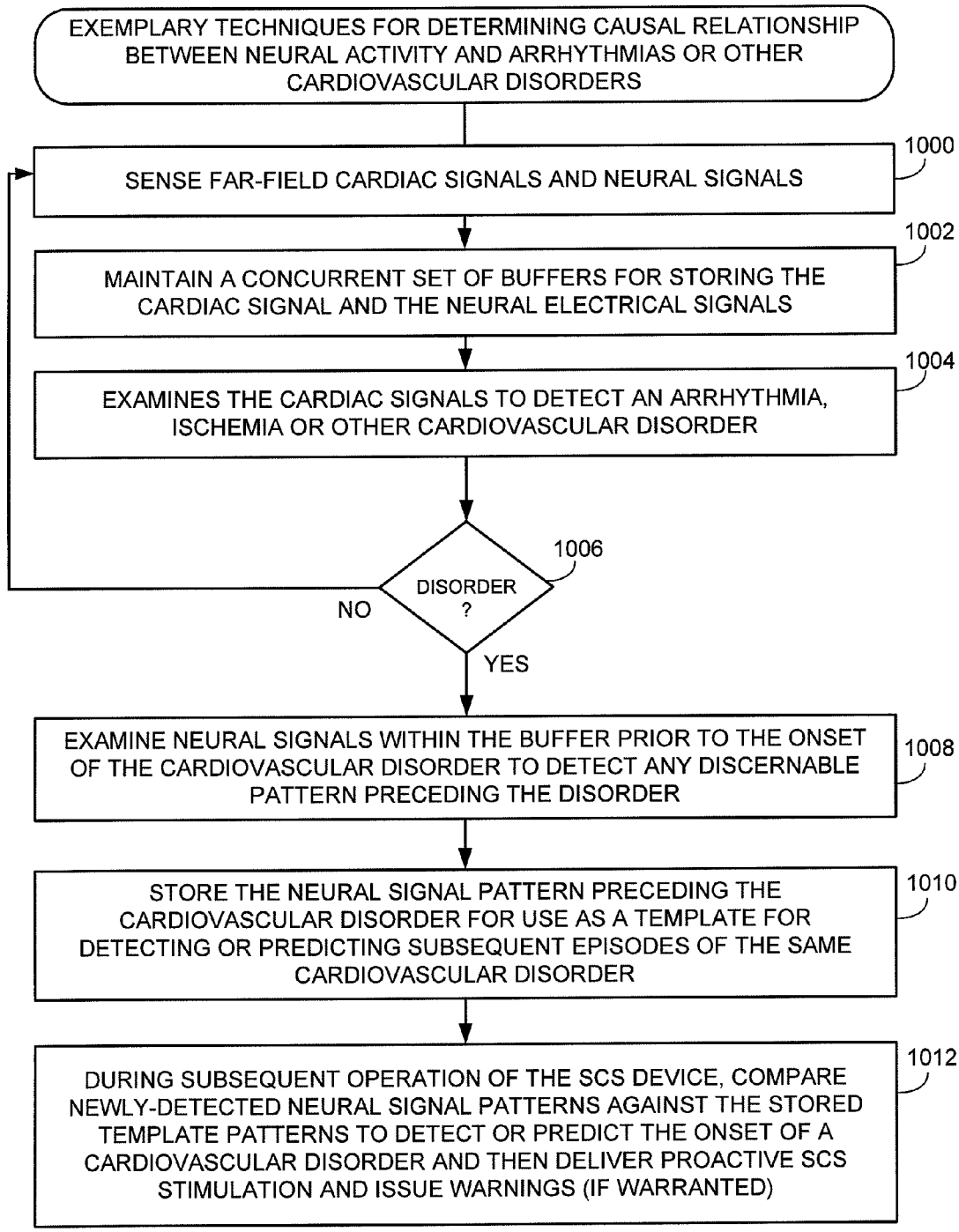
FIG. 14 illustrates an exemplary procedure for determining a causal relationship between neural activity and cardiovascular disorders within the patient for use with the general technique of FIG. 3.

FIG. 14 summarizes a technique for determining a causal relationship within the patient between neural activity and arrhythmias or other cardiovascular disorders, which may be helpful for detecting or predicting disorders, controlling proactive neurostimulation or for diagnostic purposes. At step 1000, the SCS device senses far-field cardiac signals and neural signals and, at step 1002, the device maintains a concurrent set of buffers for storing the cardiac signals and the neural electrical signals. For example, the most recent two minutes worth of data may be stored. At step 1004, the device examines the cardiac signals to detect an arrhythmia, ischemia or other cardiovascular disorder. If a cardiovascular disorder is detected at step 1006, then at step 1008 the SCS device examines the neural signals within the buffer prior to the onset of the cardiovascular disorder to detect any discernible pattern preceding the disorder. At step 1010, then SCS device stores the neural signal pattern preceding the cardiovascular disorder for use as a template for detecting or predicting subsequent episodes of that particular cardiovascular disorder. Different neural signals patterns can be stored for different arrhythmias or other cardiovascular disorders. For example, one neural pattern may be indicative of a subsequent tachycardia; whereas another might be indicative of a subsequent bradycardia; and another might be indicative of a subsequent cardiac ischemia. At step 1012, during subsequent operation of the SCS device, the device compares newly-detected neural signals to detect patterns therein indicative of an imminent arrhythmia or other cardiovascular disorder so that warnings can be generated to alert the patient or caregiver and proactive SCS stimulation can be initiated in an attempt to prevent or mitigate an ensuing cardiovascular disorder.

Figure 15:
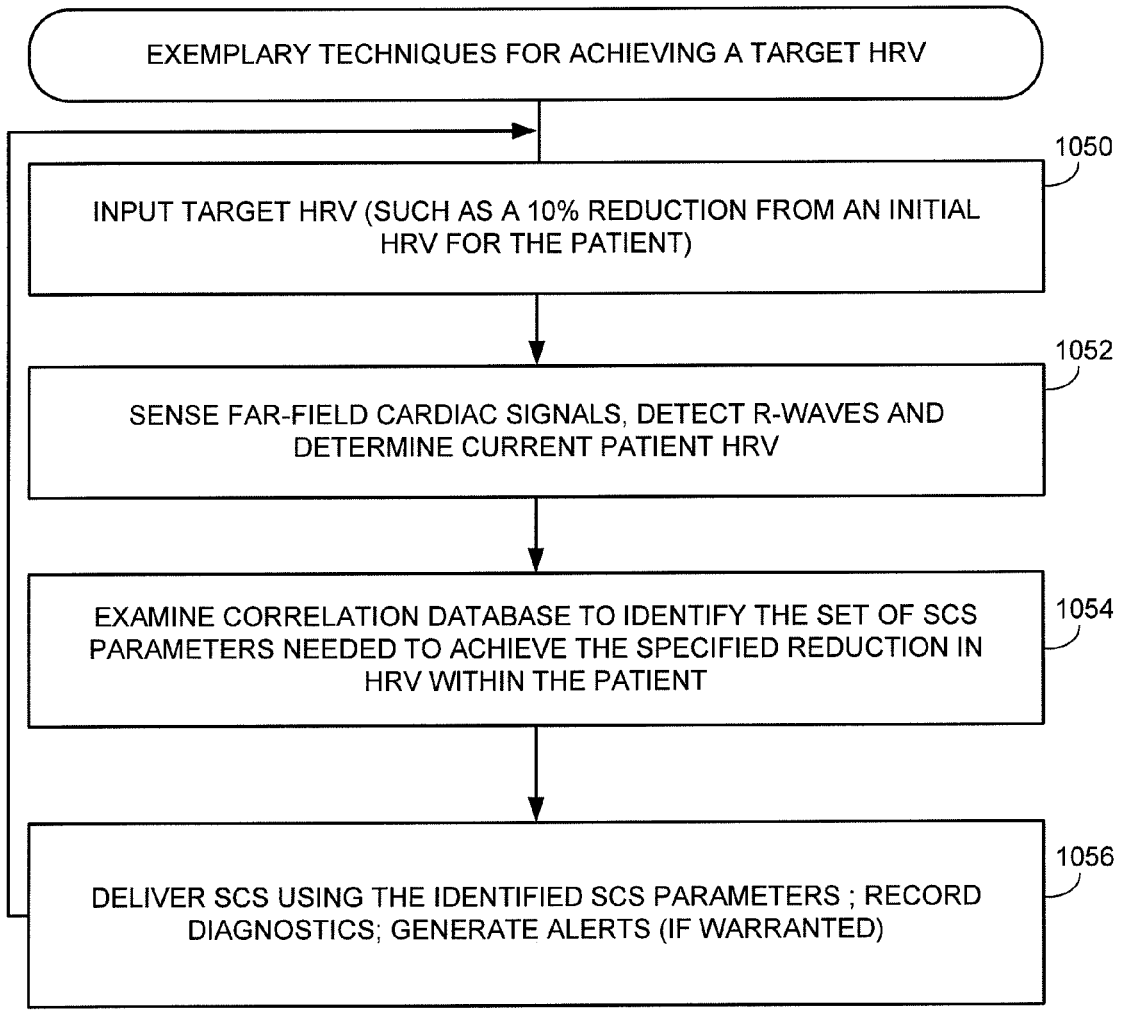
FIG. 15 illustrates an exemplary procedure for achieving a target HRV within the patient for use with the general technique of FIG. 3.

FIG. 15 briefly summarizes a general technique for achieving a target HRV within the patient. In this regard, even if no arrhythmia or other cardiovascular disorder is detected within the patient, the device can be programmed by the clinician to attempt to reach a target HRV value, such as a 10% reduction in HRV compared to a current value. To this end, at step 1050, the SCS device inputs and stores a target HRV value for the patient from the clinician. At step 1052, the device senses far-field cardiac signals, detects R-waves and determines current HRV. From this HRV value, the device can then calculate the desired HRV value based on the target reduction, such as by calculating 90% of the current HRV value for use as the target. At step 1054, the device examines the correlation database to identify the set of SCS parameters needed to achieve the target HRV value. For example, the device examines database 216 of FIG. 5 to find the configuration that achieved the target HRV then looks up the SCS parameters corresponding to that particular configuration from database 214. SCS is then delivered at step 1056 using the specified SCS control parameters in an effort to achieve the target HRV.

Figure 16:
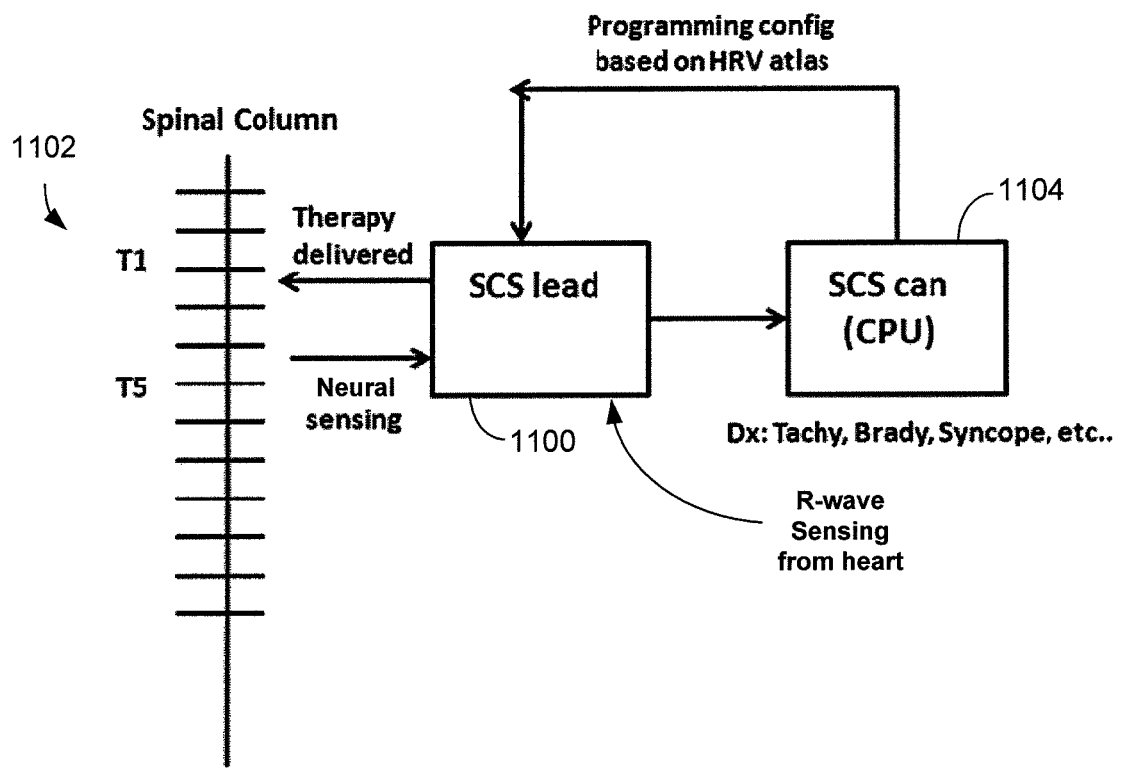
FIG. 16 provides a block diagram illustration of an overall system equipped to perform at least some of the techniques of FIGS. 3-14.

FIG. 16 provides a block diagram that broadly summarizes the general systems and techniques for controlling SCS set forth above. An SCS lead 1100 is positioned adjacent the spinal column 1102 for delivering therapy and sensing neural signals. The lead also senses R-waves from the heart. These signals are relayed to the CPU inside the can of the SCS device 1104 for processing in accordance with the techniques described above to detect tachycardia, bradycardia, syncope, etc. The SCS programming configuration is then adjusted based on the HRV mapping atlas for controlling delivering of further stimulation via the lead.

Figure 17:
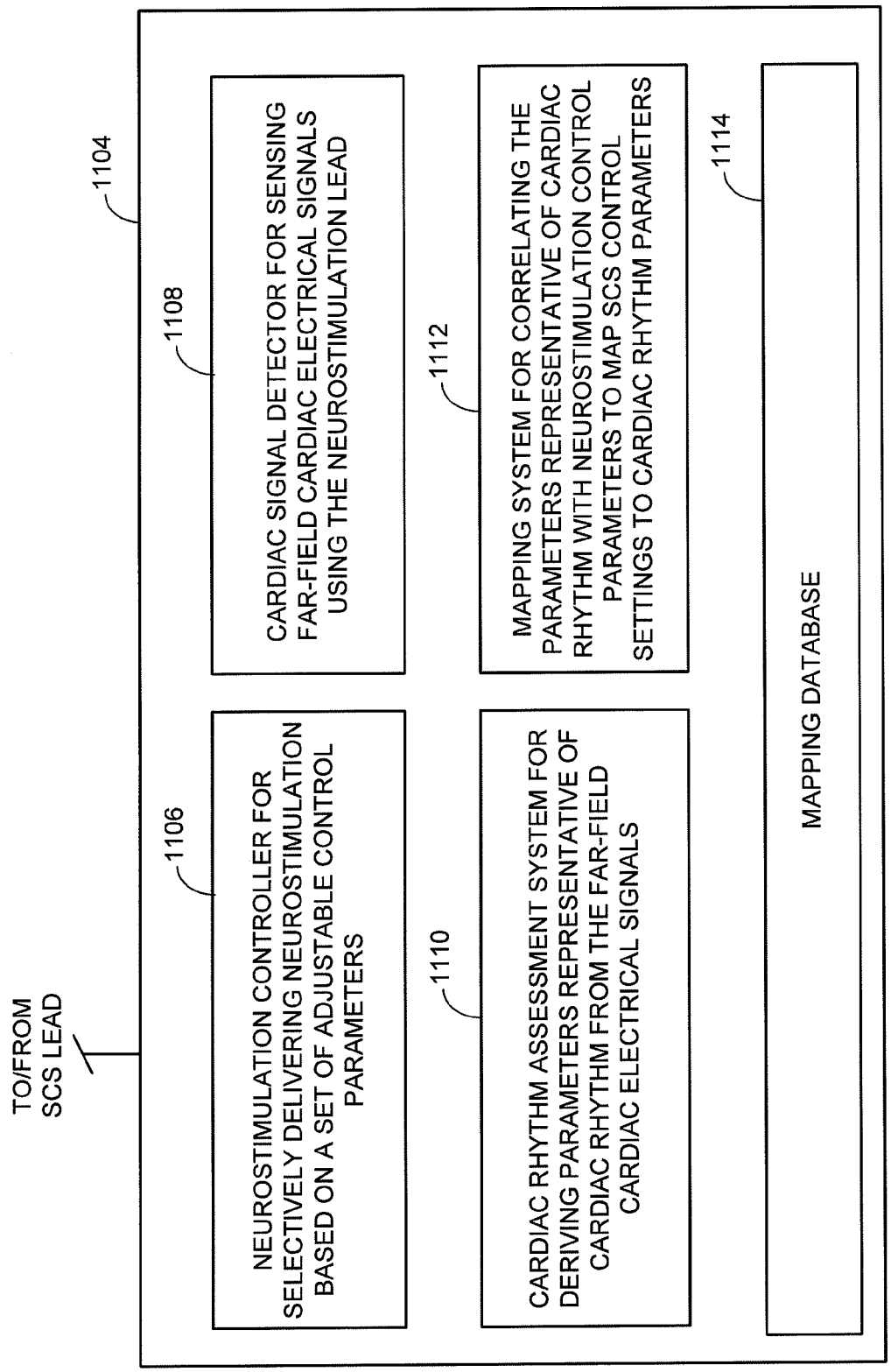
FIG. 17 provides a block diagram of pertinent components of the SCS device of FIG. 16.

FIG. 17 summarizes pertinent components of the SCS device 1104 of FIG. 16. Briefly, the device includes a neurostimulation controller 1106 operative to selectively deliver neurostimulation using the SCS lead (see, FIGS. 1 and 2) based on a set of adjustable control parameters. A neurostimulation lead-based cardiac signal detector 1108 is operative to sense far-field cardiac electrical signals using the neurostimulation lead while neurostimulation is selectively delivered using the set of adjustable control parameters. A cardiac rhythm assessment system 1110 is operative to derive parameters representative of cardiac rhythm from the far-field cardiac electrical signals sensed using the neurostimulation lead. A mapping system 1112 is operative to correlate the parameters representative of cardiac rhythm with neurostimulation control parameters to map neurostimulation control settings to cardiac rhythm parameters by exploiting a mapping database 1114. Depending upon the implementation, the various components of FIG. 17 may be implemented as separate software modules of a microcontroller, or the modules may be combined to permit a single module to perform multiple functions. In addition, some or all of these components may be implemented separately from the microcontroller, using application specific integrated circuits (ASICs) or the like.

Thus, a variety of exemplary techniques have been described for use in controlling or adjusting SCS control parameters, particularly for setting the control parameters to preferred, target or optimal values for addressing patient needs. It should be understood that any preferred, target or optimal neuromodulation control parameters obtained using techniques described herein are not necessarily absolutely optimal in a given quantifiable or mathematical sense. What constitutes "optimal" depends on the criteria used for judging the resulting performance, which can be subjective in the minds of patients and clinicians. The neuromodulation control parameters identified or selected using the techniques described herein represent, at least, a preferred set of neuromodulation control parameters. Clinicians (or in some case patients) may choose to adjust or alter the neuromodulation control parameters at their discretion using suitable external control devices.

The techniques described herein may be used, where appropriate, in conjunction with other neurostimulation techniques. See, for example, the neurostimulation techniques described in U.S. Pat. No. 8,682,450, filed Jul. 31, 2012, of Min et al., entitled "Systems and Methods for Controlling Neurostimulation of Acupuncture Sites using an Implantable Cardiac Rhythm Management Device"; U.S. Pat. No. 7,826,899 to Ryu et al., entitled "Neurostimulation and Neurosensing Techniques to Optimize Atrial Anti-Tachycardia Pacing for Termination of Atrial Tachyarrhythmias"; and U.S. Pat. No. 7,715,915 to Ryu et al., entitled "Neurostimulation and Neurosensing Techniques to Optimize Atrial Anti-Tachycardia Pacing for Prevention of Atrial Tachyarrhythmias." See, also, U.S. Patent Pub. No. 2010/0331921 of Bornzin et al., entitled "Neurostimulation Device and Methods for Controlling Same"; U.S. Patent Pub. No. 2010/0057158 of Rodriguez et al., entitled "Neurostimulation Based on Glycemic Condition"; U.S. Pat. No. 7,164,944 to Kroll et al., entitled "Analgesic Therapy for ICD Patients." SCS is also discussed, e.g., in U.S. Pat. No. 7,099,718 to Thacker, et al. Techniques for stimulating sympathetic nerves are discussed in U.S. Pat. No. 6,937,896, to Kroll, entitled "Sympathetic Nerve Stimulator and/or Pacemaker." See, also, U.S. Patent Pub. No. 2010/0312128 Karst et al., entitled "Systems and Methods for Monitoring Blood Partitioning and Organ Function"; U.S. Patent Pub. No. 2010/0161006 of Keel et al. entitled "System and Method for Monitoring Diastolic Function using an Implantable Medical Device." In at least some of these documents, systems and techniques are described for use with CRMDs but may be applicable for use with a suitably-equipped standalone SCS device as well.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical system for implant within a patient having a neurostimulation device, the method comprising:
   sensing far-field cardiac electrical signals using a lead of the neurostimulation device;
   using the lead to selectively deliver neurostimulation using a set of adjustable control parameters;
   deriving parameters representative of cardiac rhythm from the far-field cardiac electrical signals sensed using the lead of the neurostimulation device;
   correlating the parameters representative of cardiac rhythm with neurostimulation control parameters to map neurostimulation control settings to cardiac rhythm parameters; and
   controlling the delivery of further neurostimulation based on the mapping of neurostimulation control settings to cardiac rhythm parameters;
   wherein the lead of the neurostimulation device is also equipped to sense neural electrical signals and wherein sensing far-field cardiac electrical signals including distinguishing between the far-field cardiac electrical signals and the neural electrical signals; and
   wherein the device has a sense amplifier with sufficient bandwidth to sense both far-field cardiac electrical signals and neural electrical signals and wherein distinguishing between cardiac electrical signals and neural electrical signals includes selectively filtering a frequency spectrum sensed by the sense amplifier to separate far-field cardiac electrical signals from neural electrical signals.

2. The method of claim 1 wherein neurostimulation is delivered while adjusting one or more of: a neuromodulation amplitude; a neuromodulation frequency; a neuromodulation pulse width; a neuromodulation electrode configuration and a neuromodulation duration.

3. The method of claim 1 wherein distinguishing between the cardiac electrical signals and the neural electrical signals further includes one or both of: selectively switching between the cardiac sense amplifier and a neural sense amplifier and switching between different sensing vectors for cardiac sensing as opposed to neural sensing.

4. The method of claim 1 wherein sensing far-field cardiac electrical signals using the lead of the neurostimulation device is performed to detect far-field cardiac rhythm events including one or more of: atrial depolarization events (P-waves); ventricular depolarization events (R-waves); and ventricular repolarization events (T-waves) using one or more sensing vectors.

5. The method of claim 4 further including distinguishing among the cardiac rhythm events using one or more of: signal amplitude; signal slope; signal morphology; sensing vector location; and sensing electrode spacing.

6. The method of claim 5 wherein distinguishing among the cardiac rhythm events using signal morphology includes one or more of: correlating waveform templates; counting baseline crossings; and assessing event width.

7. The method of claim 1 wherein deriving parameters representative of cardiac rhythm includes detecting parameters representative of one or more of: heart rate variability (HRV), arrhythmia, prolonged QT intervals and ischemia.

8. The method of claim 7 wherein detecting parameters representative of HRV includes detecting one or more of: high frequency (HF) components of HRV; low frequency (LF)

components of HRV; very low frequency (VLF) components of HRV; and a pNN50 statistic.

9. The method of claim 7 further including detecting a causal relationship between neural activity and an arrhythmia.

10. The method of claim 9 wherein detecting the causal relationship between neural activity and an arrhythmia includes: detecting and buffering neural electrical signals; detecting an episode of an arrhythmia and, in response, examining the buffer to detect a pattern of neural electrical signals preceding the episode of arrhythmia; and storing the pattern of neural electrical signals as an arrhythmia template to detect subsequent arrhythmias.

11. The method of claim 7 wherein ischemia is detected based on an ST segment shift.

12. The method of claim 11 wherein detecting ischemia further includes: identifying a confirmed R-wave for use as a temporal reference; maintaining a detection window spanning a plurality of R-waves; detecting a shift in ST interval; examining a portion of the detection window prior to the ST segment shift; and confirming the ST segment shift based on signals within the detection window compared to the confirmed R-wave.

13. The method of claim 1 wherein the system is equipped to detect patient activity and heart rate and wherein controlling the delivery of further neurostimulation includes selecting a control setting configuration associated with an appropriate response to acute pain and then delivering further neurostimulation at the identified control setting to mitigate the acute pain.

14. The method of claim 1 wherein deriving parameters representative of cardiac rhythm includes detecting at least one parameter indicative of a cardiovascular disorder and wherein the method further includes generating a warning signals in response thereto.

15. A method for use with an implantable medical system for implant within a patient having a neurostimulation device, the method comprising:
sensing far-field cardiac electrical signals using a lead of the neurostimulation device;
using the lead to selectively deliver neurostimulation using a set of adjustable control parameters;
deriving parameters representative of cardiac rhythm from the far-field cardiac electrical signals sensed using the lead of the neurostimulation device;
correlating the parameters representative of cardiac rhythm with neurostimulation control parameters to map neurostimulation control settings to cardiac rhythm parameters; and
controlling the delivery of further neurostimulation based on the mapping of neurostimulation control settings to cardiac rhythm parameters,
wherein deriving parameters representative of cardiac rhythm includes detecting HRV and wherein correlating cardiac rhythm with neurostimulation control parameters to map neurostimulation control settings to cardiac rhythm parameters includes correlating HRV parameters to neurostimulation control parameters to generate a mapping of neurostimulation control settings to HVR, and
wherein deriving parameters representative of cardiac rhythm further includes detecting a tachycardia and wherein controlling the delivery of further neurostimulation includes examining the mapping of neurostimulation control settings to HVR to identify a control setting configure associated with a parasympathetic response and then delivering further nerostimulation using the identified control setting to achieve a parasympathetic response address the tachycardia.

16. The method of claim 15 wherein selectively delivering neurostimulation using a set of adjustable control parameters is performed using different sets of control parameters to correlate HRV parameters with the different sets of neurostimulation control parameters.

17. The method of claim 16 wherein controlling the delivery of further neurostimulation based on the mapping of neurostimulation control settings to cardiac rhythm parameters includes setting a target HRV value and then adjusting the neurostimulation control settings to achieve the target HRV.

18. The method of claim 15 wherein the parasympathetic response is associated with an HRV exhibiting one or more of: a relatively high pNN50 value; a relatively high HF value; and a relatively low LF/HF ratio.

19. The method of claim 15 wherein the further neurostimulation is delivered using an electrode positioned near one or more of C7-T2.

20. The method of claim 15 wherein deriving parameters representative of cardiac rhythm includes detecting bradycardia and wherein controlling the delivery of further neurostimulation includes examining the mapping of neurostimulation control settings to HRV to identify a control setting configuration associated with a sympathetic response and then delivering further neurostimulation using the identified control setting to achieve a sympathetic response to address the bradycardia.

21. The method of claim 20 wherein the sympathetic response is associated with an HRV exhibiting one or more of: a relatively high LF and a relatively high LF/HF ratio.

22. The method of claim 20 wherein the further neurostimulation is delivered using an electrode position near one or more of T5, T9-T10 and L1-L2.

23. The method of claim 15 wherein deriving parameters representative of cardiac rhythm includes detecting a prolonged QT interval and wherein controlling the delivery of further neurostimulation includes examining the mapping of neurostimulation control settings to HRV to identify a control setting configuration associated with an appropriate response to a prolonged QT interval to reduce arrhythmia susceptibility and then delivering further neurostimulation at the identified control setting.

24. The method of claim 15 wherein the system is equipped to detect cardiac contractility and wherein controlling the delivery of further neurostimulation includes examining the mapping of neurostimulation control settings to HRV to identify a control setting configuration associated with an appropriate response to low contractility and then delivering further neurostimulation at the identified control setting to address the low contractility.

25. The method of claim 15 wherein deriving parameters representative of cardiac rhythm includes detecting ischemia and wherein controlling the delivery of further neurostimulation includes examining the mapping of neurostimulation control settings to HRV to identify a control setting configuration associated with an appropriate response to ischemia and then delivering further neurostimulation at the identified control setting to address the ischemia.

26. The method of claim 15 further including a preliminary step for use within patients known to have coronary artery disease (CAD) of selectively delivering neurostimulation to preemptively address an ischemic insult.

27. The method of claim 15 wherein deriving parameters representative of cardiac rhythm includes detecting syncope and wherein controlling the delivery of further neurostimulation includes examining the mapping of neurostimulation control settings to HRV to identify a control setting configuration associated with an appropriate response to syncope and then delivering further neurostimulation at the identified control setting to address the syncope.

28. A method for use with an implantable medical system for implant within a patient having a neurostimulation device, the method comprising:
   sensing far-field cardiac electrical signals using a lead of the neurostimulation device;
   using the lead to selectively deliver neurostimulation using a set of adjustable control parameters;
   deriving parameters representative of cardiac rhythm from the far-field cardiac electrical signals sensed using the lead of the neurostimulation device;
   correlating the parameters representative of cardiac rhythm with neurostimulation control parameters to map neurostimulation control settings to cardiac rhythm parameters; and
   controlling the delivery of further neurostimulation based on the mapping of neurostimulation control settings to cardiac rhythm parameters,
   wherein deriving parameters representative of cardiac rhythm includes detecting PR intervals and wherein the method includes a preliminary step of delivering neurostimulation at a control setting configuration sufficient to regularize the PR intervals.

29. A method for use with an implantable medical system for implant within a patient having a neurostimulation device, the method comprising:
   sensing far-field cardiac electrical signals using a lead of the neurostimulation device;
   using the lead to selectively deliver neurostimulation using a set of adjustable control parameters;
   deriving parameters representative of cardiac rhythm from the far-field cardiac electrical signals sensed using the lead of the neurostimulation device;
   correlating the parameters representative of cardiac rhythm with neurostimulation control parameters to map neurostimulation control settings to cardiac rhythm parameters; and
   controlling the delivery of further neurostimulation based on the mapping of neurostimulation control settings to cardiac rhythm parameters,
   wherein the neurostimulation system is a spinal cord stimulation (SCS) system having an SCS lead and wherein sensing far-field cardiac electrical signals is performed by the SCS system using the SCS lead.

30. A system for use with an implantable medical system for implant within a patient having a neurostimulation device with a neurostimulation lead, the system comprising:
   a neurostimulation controller operative to selectively deliver neurostimulation using the neurostimulation lead based on a set of adjustable control parameters;
   a neurostimulation lead-based cardiac signal detector operative to sense far-field cardiac electrical signals using the neurostimulation lead;
   a cardiac rhythm assessment system operative to derive parameters representative of cardiac rhythm from the far-field cardiac electrical signals sensed using the neurostimulation lead; and
   a mapping system operative to correlate the parameters representative of cardiac rhythm with neurostimulation control parameters to map neurostimulation control settings to cardiac rhythm parameters,
   wherein the neurostimulation lead is also equipped to sense neural electrical signals and distinguish between the far-field cardiac electrical signals and the neural and electrical signals; and
   wherein the device has a sense amplifier with sufficient bandwidth to sense both far-field cardiac electrical signals and neural electrical signals and wherein the neurostimulation lead is equipped to selectively filtering a frequency spectrum sensed by the sense amplifier to separate far-field cardiac electrical signals from neural electrical signals.

31. A system for use with an implantable medical system for implant within a patient having a neurostimulation device with a neurostimulation lead, the system comprising:
   means for sensing far-field cardiac electrical signals and neural electrical signals and selectively delivering neurostimulation using a set of adjustable control parameters using a lead of the neurostimulation device;
   means for deriving parameters representative of cardiac rhythm from the far-field cardiac electrical signals sensed using the lead of the neurostimulation device;
   means for correlating the parameters representative of cardiac rhythm with neurostimulation control parameters to map neurostimulation control settings to cardiac rhythm parameters; and
   means for controlling the delivery of further neurostimulation based on the mapping of neurostimulation control settings to cardiac rhythm parameters,
   wherein the means for sensing far-field cardiac electrical signals and neural signals distinguishes between the far-field cardiac electrical signal and the neural electrical signal by selectively filtering a frequency sensed by the means for sensing far-field cardiac electrical signals and neural electrical signals.

* * * * *